(12) United States Patent
Rosa-Calatrava et al.

(10) Patent No.: US 12,285,433 B2
(45) Date of Patent: Apr. 29, 2025

(54) DILTIAZEM FOR USE IN THE TREATMENT OF MICROBIAL INFECTIONS

(71) Applicants: UNIVERSITE CLAUDE BERNARD LYON 1, Mlleurbanne (FR); CENTRE NATIONAL DE LA RECHERCHE SCIENTIFIQUE (CNRS), Paris (FR); ECOLE NORMALE SUPERIEURE DE LYON, Lyons (FR); INSTITUT NATIONAL DE LA SANTE ET DE LA RECHERCHE MEDICALE (INSERM), Paris (FR); UNIVERSITE LAVAL, Quebec (FR)

(72) Inventors: Manuel Rosa-Calatrava, Lyons (FR); Olivier Terrier, Lyons (FR); Claire Nicolas De Lamballerie, Ensues la Redonne (FR); Guy Boivin, Quebec (CA); Mario Andres Pizzorno, Lyons (FR)

(73) Assignees: UNIVERSITE CLAUDE BERNARD LYON 1, Villeurbanne (FR); CENTRE NATIONAL DE LA RECHERCHE SCIENTIFIQUE (CNRS), Paris (FR); ECOLE NORMALE SUPERIEURE DE LYON, Lyons (FR); INSTITUT NATIONAL DE LA SANTE ET DE LA RECHERCHE MEDICALE (INSERM), Paris (FR); UNIVERSITE LAVAL, Quebec (CA)

( * ) Notice: Subject to any disclaimer, the term of this patent is extended or adjusted under 35 U.S.C. 154(b) by 1090 days.

(21) Appl. No.: 17/057,141

(22) PCT Filed: May 23, 2019

(86) PCT No.: PCT/FR2019/051186
§ 371 (c)(1),
(2) Date: Nov. 20, 2020

(87) PCT Pub. No.: WO2019/224489
PCT Pub. Date: Nov. 28, 2019

(65) Prior Publication Data
US 2021/0154205 A1     May 27, 2021

(30) Foreign Application Priority Data
May 23, 2018 (FR) ...................... 1854307

(51) Int. Cl.
*A61K 31/554*     (2006.01)
*A61K 45/06*     (2006.01)
(Continued)

(52) U.S. Cl.
CPC ............ *A61K 31/554* (2013.01); *A61K 45/06* (2013.01); *A61P 31/04* (2018.01); *A61P 31/14* (2018.01); *A61P 37/04* (2018.01)

(58) Field of Classification Search
CPC .. A61K 31/554; A61K 31/7076; A61K 45/06; A61P 37/04; A61P 31/12; A61P 31/14
See application file for complete search history.

(56) References Cited

U.S. PATENT DOCUMENTS

| 4,605,552 | A | 8/1986 | Fritschi |
| 6,716,835 | B1 | 4/2004 | Picaud et al. |

(Continued)

FOREIGN PATENT DOCUMENTS

| EP | 3216453 A1 | 12/2010 | |
| JP | 2013139391 A | * 7/2013 | ........... A61K 31/198 |

(Continued)

OTHER PUBLICATIONS

Meldrum et al, J. Surgical Research, 1991, 51, 158-164.*
(Continued)

*Primary Examiner* — Eric Olson
*Assistant Examiner* — Benjamin M Brandsen

(74) *Attorney, Agent, or Firm* — Arrigo, Lee, Guttman & Mouta-Bellum LLP

(57) ABSTRACT

The present invention relates to diltiazem for use as an agent for activating the expression of at least one gene encoding a type III interferon, in the prevention and/or treatment of infections by at least one pathogenic microorganism of the epithelia of the respiratory and/or intestinal tracts.

6 Claims, 13 Drawing Sheets

(51) Int. Cl.
    *A61P 31/04*    (2006.01)
    *A61P 31/14*    (2006.01)
    *A61P 37/04*    (2006.01)

(56) References Cited

U.S. PATENT DOCUMENTS

| | | | |
|---|---|---|---|
| 11,351,180 B2* | 6/2022 | Rosa-Calatrava | A61K 45/06 |
| 2018/0042937 A1 | 2/2018 | Rosa-Calatrava | |
| 2019/0224266 A1* | 7/2019 | Lin-Shiau | A61K 31/353 |

FOREIGN PATENT DOCUMENTS

| | | |
|---|---|---|
| WO | 87/07508 | 12/1987 |
| WO | 02/094238 A1 | 11/2002 |
| WO | 2004 089283 A2 | 10/2004 |
| WO | 2005 007082 A2 | 1/2005 |
| WO | 2005 102353 A1 | 11/2005 |
| WO | 2011/066657 A1 | 6/2011 |
| WO | 2011126071 A1 | 10/2011 |
| WO | 2016/146836 A2 | 9/2016 |

OTHER PUBLICATIONS

Oxford English Dictionary, Definition of "to prevent", accessed Jan. 8, 2024. (Year: 2024).*
RSV Symptoms, US Centers for Disease Control and Prevention; https://www.cdc.gov/rsv/about/symptoms.html; page updated Mar. 7, 2017 (Accessed archive via Wayback Machine from Dec. 9, 2017 on Jan. 18, 2024). (Year: 2017).*
RSV Prevention, US Centers for Disease Control and Prevention; https://www.cdc.gov/rsv/about/prevention.html; page updated Mar. 7, 2017 (Accessed archive via Wayback Machine from Dec. 9, 2017 on Jan. 18, 2024). (Year: 2017).*
Wagner, S.; et al. "Novel Strategies for the Treatment of Pseudomonas aeruginosa Infections" 2016, J. Medicinal Chemistry, vol. 59 , pp. 5929-5969. (Year: 2016).*
Preibe, G. P.; Goldberg, J. B. "Vaccines for Pseudomonas aeruginosa: a long and winding road" 2014, Expert Reviews Vaccines, vol. 13, pp. 507-519. (Year: 2014).*
Johansen, H. K.; Gøtzsche, P. C. "Vaccines for preventing infection with Pseudomonas aeruginosa in cystic fibrosis" 2013, Cochrane Database of Systematic Reviews, Issue 6. Art. No. CD001399. (Year: 2013).*
English language translation of JP2013139391A, published 2013 (translated Jan. 10, 2024). (Year: 2013).*
English language translation of WO2016146836A2, published 2016 (translated Jan. 19, 2024). (Year: 2016).*
Kruszewska, H.; et al. "Estimation of antimicrobial activity of selected non-antibiotic products" 2006, Acta Pol. Pharm., vol. 63, pp. 457-460. (Year: 2006).*
Lai, A. L.; et al. "The SARS-COV Fusion Peptide Forms an Extended Bipartite Fusion Platform that Perturbs Membrane Order in a Calcium-Dependent Manner" 2017, J. Mol. Biol., vol. 429, pp. 3875-3892. (Year: 2017).*
Shahrabadi, M. S.; Lee, P. W. K. "Calcium Requirement for Syncytium Formation in HEp-2 Cells by Respiratory Syncytial Virus" 1988, J. Clin. Microbiol., vol. 26, p. 139-141. (Year: 1988).*
Leyrat, C.; et al. "Structure and Self-Assembly of the Calcium Binding Matrix Protein of Human Metapneumovirus" 2014, Structure, vol. 22, p. 136-148. (Year: 2014).*
Andreakos E, Salagianni M, Galani IE, Koltsida O. Interferon-λs: Front-Line Guardians of Immunity and Homeostasis in the Respiratory Tract. Front Immunol. Sep. 29, 2017;8:1232.
Galani IE, Triantafyllia V, Eleminiadou EE, Koltsida O, Stavropoulos A, Manioudaki M, Thanos D, Doyle SE, Kotenko SV, Thanopoulou K, Andreakos E. Interferon-λ Mediates Non-redundant Front-Line Antiviral Protection against Influenza Virus Infection without Compromising Host Fitness. Immunity. May 16, 2017;46(5):875-890.e6.
Chan HLY, Ahn SH, Chang TT, Peng CY, Wong D, Coffin CS, Lim SG, Chen PJ, Janssen HLA, Marcellin P, Serfaty L, Zeuzem S, Cohen D, Critelli L, Xu D, Wind-Rotolo M, Cooney E; LIRA-B Study Team. Peginterferon lambda for the treatment of HBeAg-positive chronic hepatitis B: A randomized phase 2b study (LIRA-B). J Hepatol. May 2016;64(5):1011-1019.
Davidson S, McCabe TM, Crotta S, Gad HH, Hessel EM, Beinke S, Hartmann R, Wack A. IFNλ is a potent anti-influenza therapeutic without the inflammatory side effects of IFNα treatment. EMBO Mol Med. Sep. 1, 2016;8(9):1099-112.
Donnelly RP, Kotenko SV. Interferon-lambda: a new addition to an old family. J Interferon Cytokine Res. Aug. 2010;30(8):555-64.
Kotenko SV, Gallagher G, Baurin VV, Lewis-Antes A, Shen M, Shah NK, Langer JA, Sheikh F, Dickensheets H, Donnelly RP. IFN-lambdas mediate antiviral protection through a distinct class II cytokine receptor complex. Nat Immunol. Jan. 2003;4(1):69-77.
O'Brien TR, Prokunina-Olsson L, Donnelly RP. IFN-λ4: the paradoxical new member of the interferon lambda family. J Interferon Cytokine Res. Nov. 2014;34(11):829-38. doi: 10.1089/jir.2013.0136.
Yoichiro Fujioka and al, Cell Host & Microbe, vol. 23(6), 809-818, 2018.
Meldrum D R and al, Journal of Surgical Research, vol. 51(2), 158-164, 1991.
Walid F.Elkhatib and al, Journal of Infection and Public Health, vol. 1(2), 105-112, 2008.

* cited by examiner

4D

4E

A

B

HMPV
MOI 0.1 J4
Objectif x20

HMPV treated with 90µM diltiazem
MOI 0.1 J4
Objective x20

8A

Induction of IFNL2 gene expression induced by diltiazem treatment in mice at day 5

8B

DILTIAZEM FOR USE IN THE TREATMENT OF MICROBIAL INFECTIONS

FIELD OF THE INVENTION

The present invention relates to a compound for use in the prevention and/or treatment of infections by pathogenic microorganisms.

More particularly, the present invention relates to a compound for use in the prevention and/or treatment of infections by pathogenic microorganisms of the epithelia of the respiratory and/or intestinal tracts.

PRIOR ART

Infections by Pathogenic Microorganisms of the Epithelia of the Respiratory and/or Intestinal Tracts Acute respiratory infections (ARI) are one of the main causes of consultations, hospitalizations and deaths worldwide, being in particular the leading cause of death in young children with nearly 2 million deaths per year. Each year, to try to treat these various respiratory infections, the cost to society is estimated at between 1.5 and 2 billion euros.

Among the etiological agents responsible for ARI, viruses dominate. They are found in most cases of childhood pneumonia and are a predisposing factor for bacterial pneumonia in adults. The most representative viruses in terms of frequency and morbidity include influenza A and B viruses, which are also a recurrent pandemic risk factor, as well as respiratory syncytial virus (hRSV or hVRS), parainfluenza viruses (hPIV) and human metapneumovirus (hMPV). Furthermore, the emergence of novel viruses of the family Coronaviridae, such as SARS and the recently described MERS-CoV virus, is highly likely to be a serious emerging health problem.

Other agents responsible for ARI are bacteria. The most representative pathogenic bacteria include *S. pneumonia, P. aeruginosa, S. aureus* and *H. influenza*. These pathogenic bacteria are etiological agents which contribute to increased co-morbidity and co-mortality in respiratory co-infections and are responsible for the emergence and increasing spread of antibiotic-resistant bacterial strains that fundamentally challenge the efficacy of conventional antibiotic treatments in both humans and animals.

With the exception of influenza viruses, there is currently no vaccine or antiviral molecule that is effective in preventing or treating infections by these various respiratory pathogenic viruses. Moreover, in the case of influenza viruses, the delivery schedule and the variable efficacy of vaccination, as well as the increasing emergence of viruses resistant to antivirals, are today very concerning.

There is currently no specific vaccine or treatment against respiratory syncytial virus (hRSV) and human metapneumovirus (hMPV). These viruses of the family Pneumoviridae are enveloped viruses (150 to 600 nm), which have a non-segmented single-stranded negative RNA genome. Phylogenetic analysis of the genes encoding the F and G proteins allows hMPVs, like hRSVs, to be divided into two main groups A and B, respectively, and to subdivide each of these groups into two subgroups A1, A2, E1 or B2. The pathologies associated with these pneumoviruses are mainly pediatric bronchiolitis, cold and flu-like illness in adults, or severe pneumonia in elderly or immunosuppressed patients.

Similarly, there is currently no specific vaccine or treatment against human parainfluenza virus (hPIV). These viruses, discovered in the late 1950s, are enveloped viruses (150 to 250 nm), which have a single-stranded negative RNA genome, belonging to the family Paramyxoviridae. They are genetically and antigenically divided into 4 types (1 to 4). Other major subtypes of hPIV-4 (A and B) and of subgroups/genotypes of hPIV-1 and hPIV-3 have been described. The hPIV-1 to hPIV-3 viruses are major causes of lower respiratory infections in infants, young children, immunosuppressed individuals, the chronically ill and the elderly. They can cause pneumonia in particular.

With respect to antibiotic resistance of the pathogenic bacteria responsible for superinfections, the European Centre for Disease Control estimates that 25 000 deaths per year in Europe result from antibiotic resistance. An equivalent excess mortality is observed in the United States by the CDC in Atlanta. The increase in resistance is believed responsible for a dramatic increase in these numbers as modeled in the report by Lord J. O'Neil on the impact of antibiotic resistance by 2050.

In February 2017, the WHO published a list of resistant bacteria that represent a global threat: *P. aeruginosa* represents, among others, a critical emergency because it is resistant to a large number of antibiotics; *S. pneumoniae* and *S. aureus*, which are resistant to methicillin (MRSA), are responsible for various lung and bone infections, as well as septicemia, particularly in the most sensitive patients.

Among these bacteria, *Pseudomonas aeruginosa* is a Gram-negative bacillus found in the environment and in more than 50% of the respiratory tracts of hospitalized patients. *P. aeruginosa* is a ubiquitous microorganism that has the ability to survive in multiple environmental conditions. This microorganism not only causes diseases in plants and animals, but also in humans, causing serious infections in immunosuppressed cancer patients and patients suffering from severe burns or cystic fibrosis.

Standard antibiotic therapy for *Pseudomonas aeruginosa* infections combines a beta-lactam (ceftazidime, imipenem or meropenem, piperacillin/tazobactam) with an aminoglycoside (tobramycin, amikacin) and/or a fluoroquinolone. The emergence of multi-resistant strains of *Pseudomonas aeruginosa* (resistance to all antibiotics of at least two of the three main classes: beta-lactams, aminoglycosides, fluoroquinolones) poses the problem of the choice of antibiotics, as the therapeutic arsenal remains very limited.

Thus, the development of new prophylactic and therapeutic treatments is a major public health objective. The success of new strategies for treating infections by these pathogens is largely based on a better characterization of their cell biology and their molecular and functional interactions with their host.

Intestinal infections are also a major cause of hospitalizations and in certain cases death. In developed countries, the most common causes of acute gastroenteritis in immunocompetent adults are noroviruses and rotaviruses, as well as the following species and genera of bacteria: *Campylobacter* spp., *Salmonella* spp., *Escherichia coli, Staphylococcus aureus, Bacillus cereus*, and *Clostridium difficile*.

Type III Interferons

Type III interferons, also known as lambda (λ) interferons, constitute the first line of antimicrobial defense in the epithelium of the respiratory and intestinal tract by contributing to the initial inhibition of pathogen dissemination, without triggering an inflammatory response (Andreakos et al., 2017). These type III interferons are effectively produced very early in response to pathogen activation of the host's cellular sensors, such as Toll-like receptors or cytoplasmic effectors. These type III interferons activate the expression of numerous so-called interferon-stimulated genes (ISGs) (via activation of the JAK/STAT pathways), which confer inhibitory activity against respiratory pathogens, by inactivating for example the cellular entry of viruses (IFITM gene) or their replication (OAS, OASL, IFIT1, IFIT2, IFIT13, ISG15 gene).

This early antipathogenic response, known as the "type III interferon" response, is notably predominant in the initial innate response of the respiratory epithelium to infection by influenza viruses (Galani et al., 2017).

Type III interferons have already been evaluated in clinical trials for the treatment of hepatitis B and C infections and have demonstrated less significant side effects compared to treatments with type I interferon (Chan et al., 2016). The use of type III interferons as a non-inflammatory antiviral treatment for influenza virus infections has recently been proposed (Davidson et al., 2016).

It would be advantageous to stimulate the endogenous production of one or more type III interferons to fight infections of epithelia of the respiratory and/or intestinal tracts, particularly viral infections of these epithelia.

However, at present, no therapeutic compound with this stimulatory activity is known. Thus, only the administration of exogenous type III interferon has been tested so far.

Diltiazem, a Calcium Channel Blocker

Diltiazem is a molecule of the benzothiazepine family, listed under CAS number 42399-41-7. This molecule can be in the form of two enantiomers L-cis and D-cis, or a racemic mixture. Diltiazem has been known for more than 30 years and is approved in Europe and in the United States by the drug regulatory authorities. It can be administered in the form of diltiazem hydrochloride. Cardizem®, Cartia®, Taztia® and Dilacor® are its most common trade names. A number of formulations are available, in particular sustained-release formulations. Diltiazem is available in various galenic forms, such as in cream form for topical application, in tablet or capsule form for oral administration, in powder form for preparation of an injectable solution or in the form of pharmaceutical preparations for inhalation (WO 02/094238, U.S. Pat. No. 4,605,552).

Its known physiological action is the inhibition of calcium channels, and thus the inhibition of intracellular calcium flow. In particular, diltiazem inhibits the entry of transmembrane calcium into the myocardial muscle fiber and the smooth muscle fiber of the vessels. This decreases the intracellular calcium concentration reaching the contractile proteins.

In humans, the administration of diltiazem is indicated for its vasodilatory action, with the goal of reducing cardiac work. It is thus used in the management of cardiac and circulatory disorders such as angina pectoris, hypertension, myocardial ischemia and tachycardia.

Other therapeutic uses of diltiazem have also been proposed in the literature, although no drugs have been approved by regulatory authorities for these new therapeutic applications.

International application WO 87/07508 describes the use of therapeutic compounds that inhibit calcium influx into the cell, such as diltiazem, for the treatment of viral infections related to cytomegalovirus or to herpes.

International application WO 2011/066657 describes the use of a calcium channel blocker, such as verapamil or diltiazem, for the treatment or prevention of viral and/or bacterial infections or autoimmune diseases. The viruses concerned are in particular oral herpes, genital herpes and herpes zoster.

International application WO 2011/126071 describes the use of compounds that inhibit calcium influx into the cell, such as diltiazem, for the treatment of viral infections, particularly those related to influenza viruses. It is specifically explained that diltiazem inhibits the interaction between the virus and calcium channels, thereby blocking the entry of the virus into cells.

International application WO 2016/146836 discloses pharmaceutical or veterinary compositions containing diltiazem for use in the prevention and/or treatment of influenza virus infection.

Patent EP 1 117 408 describes the use of diltiazem, as a calcium channel blocker compound, to treat pathologies related to the degeneration of retinal photoreceptors.

However, all the beneficial actions of diltiazem have probably not yet been explored, and the technical effects associated with diltiazem as a drug are in all likelihood not all known at this time.

DISCLOSURE OF THE INVENTION

The technical problem underlying the present invention relates to the identification of molecules for stimulating the expression of genes encoding type III interferon proteins, with the aim of preventing and/or treating infections by pathogenic microorganisms of the epithelia of the respiratory and/or intestinal tracts.

Indeed, in case of infection by microorganisms of the respiratory and/or intestinal tracts, it is advantageous to stimulate the body's response against these pathogens, without however inducing an inflammatory response, and thus avoid over-stimulation of the immune system.

At present, however, no therapeutic compound with this activity is known.

Therapeutic compounds with the ability to stimulate the expression of genes encoding proteins such as interleukin 29, interleukin 28A and/or interleukin 28B are therefore being actively sought.

Surprisingly, the inventors have demonstrated the fact that diltiazem, a calcium channel blocker, also has a stimulatory action on the expression of these genes encoding type III interferon proteins, both in vitro and in vivo.

Moreover, the inventors have demonstrated the fact that diltiazem activates the expression of a group of so-called interferon-stimulated genes (ISGs), known to be activated by type I and III interferons. The proteins encoded by ISGs are involved in antimicrobial action and/or participate in "interferon" signaling.

Thus, diltiazem can be used for various therapeutic applications, and in particular to prevent and/or treat infections by at least one pathogenic microorganism of the epithelia of the respiratory and/or intestinal tracts.

Diltiazem, in its capacity as an agent that activates the expression of genes encoding one or more type III interferon (s), is particularly suitable for the treatment of viral or bacterial infections, but also of co-infections linked to the presence of at least one virus and at least one bacterium, or of at least two viruses, or of at least two bacteria, and is particularly suitable for the treatment of bacterial superinfections concomitant with a primary viral infection.

The present invention relates to diltiazem for use as an agent for activating the expression of at least one gene encoding a type III interferon.

As the person skilled in the art knows, in view of the abundant scientific literature on the subject, activation of the "interferon III pathway" makes it possible to treat many physiological disorders, and in particular those related to infections by pathogens.

In particular, the present invention relates to diltiazem for use as an agent for activating the expression of at least one gene encoding a type III interferon, in the prevention and/or treatment of infections by at least one pathogenic microorganism of the epithelia of the respiratory and/or intestinal tracts.

The present invention also relates to diltiazem for use as an agent for activating the expression of at least one so-called ISG, in the prevention and/or treatment of infections by at least one pathogenic microorganism of the epithelia of the respiratory and/or intestinal tracts.

The present invention also relates to a pharmaceutical or veterinary composition comprising diltiazem as an agent for activating the expression of at least one gene encoding a type III interferon, for use in the prevention and/or treatment of infections by pathogenic microorganisms of the epithelia of the respiratory and/or intestinal tracts.

According to a particular aspect, the pharmaceutical or veterinary composition is characterized in that it is in a galenic form suitable for administration by inhalation.

1A—Expression ratios of the genes encoding the type III interferons IFN-λ1, IFN-λ2 and IFN-λ3 (denoted IFNL1, IFNL2 and IFNL3, respectively) determined by RNAseq between:
  reconstituted human respiratory epithelia (MucilAir® HAE, Epithelix) treated for 3 days with diltiazem (90 µM, 3 administrations in total) via their culture medium at their basolateral pole and
  untreated reconstituted human respiratory epithelia (basal level of expression of 1).

1B—Expression ratios of genes encoding IF144L, IFIT1, IFIT2, IFIT3, IFITM1, ISG15, MX1, MX2, OAS1, OAS2, OAS3, OASL, RSAD2 and STAT1 determined by RNAseq between:
  reconstituted human respiratory epithelia treated for 3 days with diltiazem (90 µM, 3 administrations in total) via their culture medium at their basolateral pole and
  untreated reconstituted human respiratory epithelia (basal level of expression of 1).

Only genes displaying an expression differential greater than or equal to 2, and a corrected p-value less than 0.05, were considered in the rest of the analysis.

1C—Expression of the IFNL1 gene induced by apical diltiazem treatment of the 3D model of reconstituted human respiratory epithelium of nasal origin.

Reconstituted human respiratory epithelia (MucilAir® HAE, Epithelix) were treated or untreated (mock) with a single dose of 90 µM diltiazem administered by the apical pole at D0. At 24 hours post-treatment, the cells were lysed and total RNA was extracted. After reverse transcription, the expression of the IFNL1 gene was measured in RT-qPCR (TaqMan, Thermo Fisher Scientific). The data were normalized using the housekeeping gene GAPDH. Expression ratios were calculated using calculations based on the 2∆∆Ct method (Livak and Schmittgen, 2001).

Figure 2:
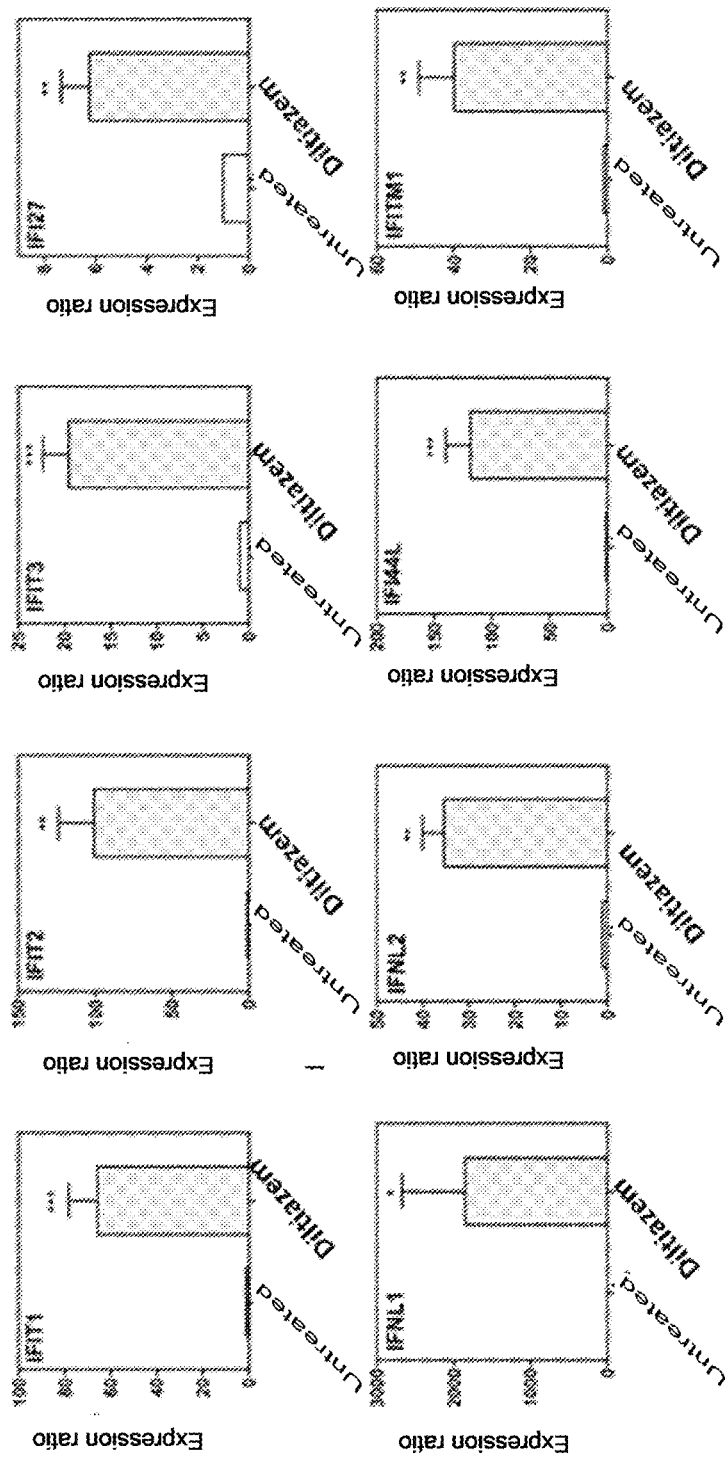

FIG. 2: Confirmation by Rt-qPCR of the induction by diltiazem of 8 genes associated with the type III interferon response.

Expression ratios of the IFIT1, IFIT2, IFIT3, IF127, IFN-λ1 (IFNL1), IFN-λ2 (IFNL2), IF144L and IFITM1 genes between:
  reconstituted human respiratory epithelia treated for 3 days with diltiazem via their basolateral pole (90 µM) (right column on the graphs) and
  untreated reconstituted human respiratory epithelia (right column on the graphs).

*p<0.05, p<0.01, *p<0.001 and ****p<0.0001 compared with untreated epithelia.

Figure 3:
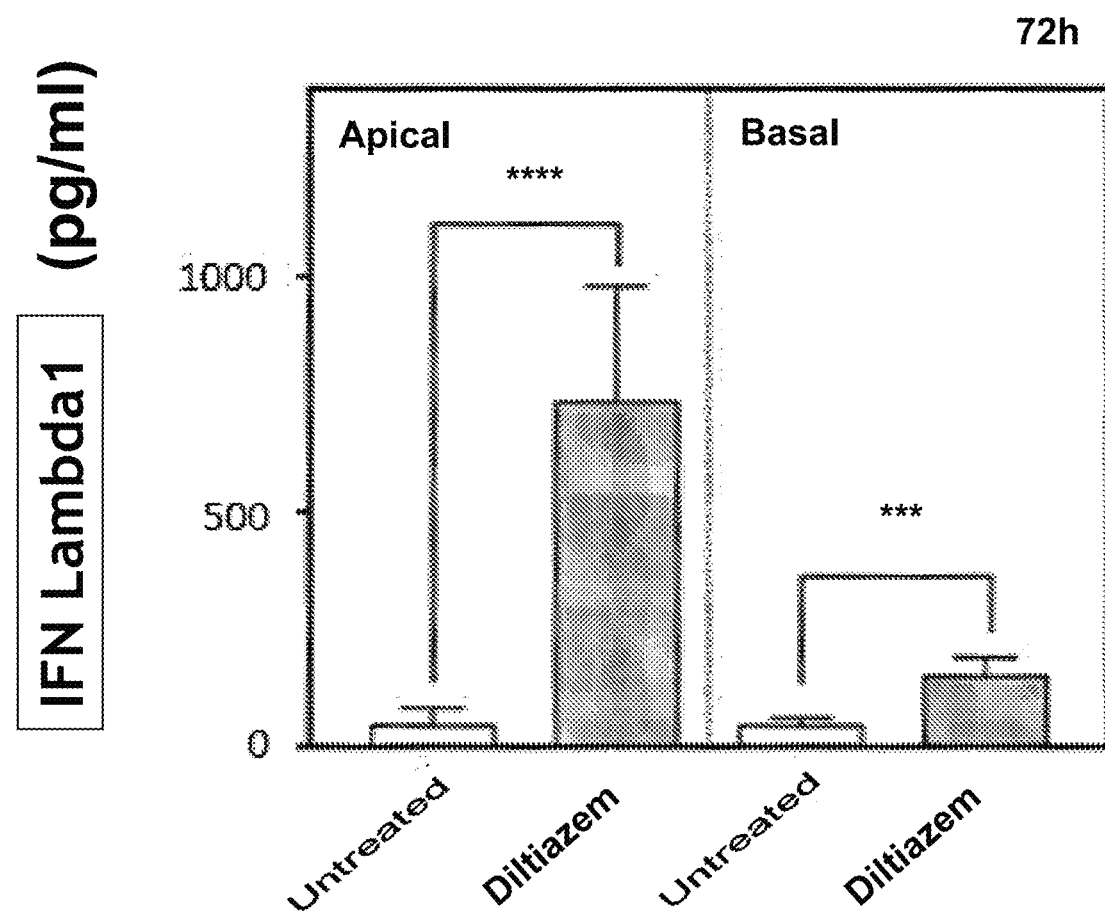

FIG. 3: ELISA measurement of interferon lambda 1 (IL-29) secretion.

Secretion levels (pg/mL) of interferon lambda 1 (IL-29) at the apical and basolateral poles of reconstituted human respiratory epithelia treated and untreated with diltiazem via their basolateral pole (90 µM, 3 administrations in total for 3 consecutive days), were measured by ELISA after 72 h of treatment.

*p<0.05, p<0.01, *p<0.001 and ****p<0.0001 compared with untreated epithelia.

FIG. 4. Diltiazem treatment reduces respiratory syncytial virus (RSV) replication within infected reconstituted human respiratory epithelia (MucilAir® HAE, Epithelix) and in a BALB/c mouse model after challenge infection (in vivo).

4A—Schematic representation of the chronology of treatments via the basolateral pole of human respiratory epithelia: after RSV infection (day 0), reconstituted epithelia are treated or not (untreated) at 5 h post-infection (5 hpi) then daily for the next three days (1, 2 and 3 days pi) with diltiazem. Viral quantification is performed at 6 days pi.

4B—Quantification by RT-qPCR of the RSV viral genome copy number (by quantifying the copies of the F gene) in relation to the total amount of RNA, at the apical pole of treated or untreated epithelia, i.e. in the culture supernatant of the epithelia.

4C—Quantification by RT-qPCR of the RSV viral genome copy number (by quantifying the copies of the F gene) in relation to the total amount of RNA within treated or untreated epithelia.

4D—Schematic representation of the chronology of infection and of treatments per os (p.o.) of mice: after RSV infection (5.105 PFU/mouse, day 0), the mice were treated or not (PBS control group) at 5 h post-infection (5 hpi) and then daily on the following two days (1 and 2 days pi) with ribavirin (40 mg/kg intraperitoneally/mouse) or daily on the following four days (1, 2, 3 and 4 days pi) with diltiazem (50 mg/kg per os/mouse). Pulmonary viral quantification is performed at 5 days pi.

4E—Quantification by RT-qPCR of the RSV viral genome copy number (by quantifying the copies of the F gene) in relation to the total amount of RNA extracted from the lungs of mice treated with ribavirin (RSV RIB) or diltiazem (RSV DIL) and untreated (RSV PBS) at 5 days after infection (days pi).

FIG. 5. Diltiazem treatment reduces human parainfluenza virus (hPIV) replication in the reconstituted human respiratory epithelium model (MucilAir® HAE, Epithelix).

5A—Schematic representation of the chronology of treatments via the basolateral pole of human respiratory epithelia: after infection by the hPIV-3 virus at an MOI of 0.1 (day 0), reconstituted epithelia are treated or untreated (untreated) at 5 h post-infection (5 hpi), then daily for the next four days (24, 48, 72 and 96 hours pi) with diltiazem. Viral quantification is performed at 120 hours pi by infectious titration (TCID50/mL).

5B—At 96 h (top) and 120 h (bottom) post-infection, the cytopathic effects induced by the hPIV-3 virus are greater and easily visible under the microscope in untreated reconstituted human respiratory epithelia (images at left), unlike those treated with diltiazem (images at right).

5C—Transepithelial electrical resistance (TEER), which reflects the integrity of the epithelium, was measured once a day from 48 h post-infection to 120 hours post-infection. Absent treatment, the TEER values of infected reconstituted human respiratory epithelia decreased significantly, from 24 h post-infection, unlike those treated with diltiazem.

5D—Viral titers (TCID50/mL) of samples taken at the apical pole of the epithelia were determined in LLC-MK2 cells from washings taken from 48 h post-infection to 120 hpi. Absent treatment, viral titers measured at the apical surface of reconstituted human respiratory epithelia peaked at 72 h post-infection at a value of roughly $10^8$ TCID50/mL and at 96 h post-infection at a value of $10^7$ TCID50/mL, unlike reconstituted human respiratory epithelia treated with diltiazem, which show significantly lower values at 72 h post-infection (roughly $10^6$ TCID50/mL) and 96 h post-infection ($10^5$ TCID50/mL).

FIG. 6. Diltiazem treatment reduces bacterial infection by *Pseudomonas aeruginosa* in a reconstituted human respiratory epithelium model (MucilAir® HAE, Epithelix).

6A—Schematic representation of the chronology of treatments of human respiratory epithelia: reconstituted human respiratory epithelia were treated 24 hours prior to infection with 90 µM diltiazem via their basolateral medium or alternatively with 10 µL of diltiazem (90 µM) at their apical surface, then infected with *Pseudomonas aeruginosa* (PAK strain) at an MOI of 1 and again treated with diltiazem 2 hours after infection under the same conditions, respectively.

6B—Under these experimental conditions (n=2), the number of bacteria collected from the apical surface of human respiratory epithelia at 24 hours post-infection was significantly lower than the number of bacteria collected from the apical surface of human respiratory epithelia treated with diltiazem in basolateral medium (115 and 106 vs 76 and 106 CFU, respectively,* p<0.05).

6C—In the context of apical treatment with diltiazem, a similar effect on *Pseudomonas aeruginosa* was observed at 24 hours post-infection (n=2), with a decrease in bacteria harvested from the apical surface of human respiratory epithelia treated with diltiazem compared with those untreated (87 and 106 versus 63.5 and 106 CFU, respectively).

FIG. 7. Diltiazem treatment reduces human metapneumovirus (hMPV) replication in a reconstituted human respiratory epithelium model (MucilAir® HAE, Epithelix).

7A—Schematic representation of the chronology of treatments of human respiratory epithelia: after infection by a recombinant hMPV-GFP virus (strain C-85473) at an MOI of 0.1, the epithelia were treated (via their basolateral medium) or not (3 epithelia per condition), by 3 successive doses of diltiazem at 90 µM at D0 (5 hpi), D1 and D3 post-infection. Viral quantification is performed at 3 days pi (supernatant) and at 5 days pi (total epithelium).

7B—Epifluorescence microscopy observations were performed at D4 post-infection to observe the impact of diltiazem treatment on viral replication. Absent treatment, a fluorescence corresponding to the viral expression of GFP is observed at D4 post-infection in almost all the epithelium (left image), whereas there are only very few fluorescent cells in the infected epithelium treated with diltiazem at the same time post-infection (right image).

7C—On Day 3 post-infection, a wash at the apical pole of the infected epithelia, treated or not with diltiazem, was performed in order to harvest the viral progeny produced. The genomic viral RNA was extracted and quantified by RT-qPCR (Biosystems™ PowerUp™ SYBR™ Green, Thermo Fisher Scientific) using a plasmid containing the HMPV N gene. The results are expressed in copies of the viral N gene/pg total RNA extracted.

7D—On Day 5 post-infection, epithelial cells were harvested and lysed to extract total RNA. The total RNAs corresponding to the hMPV N viral gene were quantified by RT-qPCR (Biosystems™ PowerUp™ SYBR™ Green, Thermo Fisher Scientific), using a plasmid array containing the HMPV N gene. The results are expressed in copies of the N gene/µg total RNA extracted.

FIG. 8: Diltiazem induction of IFN-12 (IFNL2) gene expression in vivo after nasal instillation in BALB/c mice 8A—Schematic representation of the chronology of treatments by intranasal (i.n.) instillation of BALB/c mice: the mice are treated (20 mg/kg) or not ("mock-treated" PBS control group) at day 0 (D0), then treated or not either daily on the following two days (D0, D1 and D2) or every 48 hours until day 4 (D0, D2 and D4). At D5, the nasal cavities were removed after euthanasia of the animals.

8B—The expression of the IFN-λ2 (IFNL2) gene was measured by RT-qPCR and is represented as the ratio of expression to basal level (equal to 1) of gene expression measured in untreated mice (Mock-treated).

DETAILED DESCRIPTION OF THE INVENTION

The present invention relates to a new therapeutic use of a known drug, diltiazem, a molecule of the benzothiazepine family, listed under CAS number 42399-41-7, of formula (1):

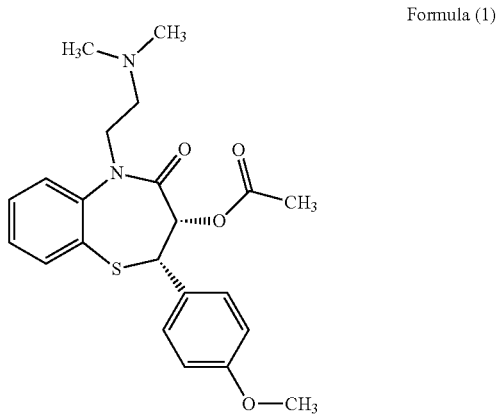 [SMILES: COc1ccc([C@@H]2Sc3ccccc3N(CCN(C)C)C(=O)[C@@H]2OC(C)=O)cc1]

Formula (1)

In the context of the present invention, the term "diltiazem" means diltiazem in all its forms, in particular in the form of salts and in particular in the form of diltiazem hydrochloride. This term includes the racemic mixture as well as each of the enantiomers when they are isolated. This term also includes diltiazem derivatives, i.e. molecules derived from formula (1), having the same biological activity of stimulating the expression of type III interferon proteins.

The present invention relates to diltiazem for use as an agent for activating the expression of at least one gene encoding a type III interferon.

Until now, diltiazem has been used for its calcium channel inhibitory action; by this inhibition of intracellular calcium transport, the administration of diltiazem generates numerous physiological effects on human and animal organisms.

The inventors have demonstrated a new technical effect of diltiazem, namely the activation of the expression of one or more genes encoding type III interferons.

According to a preferred aspect of the invention, the gene(s) whose expression is activated are endogenous genes, i.e. genes native to the organism under consideration, which have not undergone any genetic modification.

The skilled person is familiar with the involvement of type III interferons in different physiological situations and can conclude, from the scientific literature, the therapeutic potential of such a compound that activates the expression of type III interferons. In particular, cells sensitive to the effects of type III interferons, i.e. cells expressing their receptors, have been identified in the literature. Thus, the human and animal pathologies that can benefit from the use of diltiazem will be easily determined by persons skilled in the art.

More precisely, the present invention relates to diltiazem for use as an agent for activating the expression of genes encoding interleukin 29, interleukin 28A and interleukin 28B.

Thus, for the first time, a therapeutic compound for activating the "interferon III pathway", i.e. an agent that activates the expression of one or more genes encoding type III interferons, has been identified. It is the first compound with this activity to be identified.

Type III Interferons

Type III Interferons, also known as lambda ($\lambda$) interferons, constitute the first line of defense of a human or animal organism against infection by pathogenic microorganisms.

This new family of interferons, described for the first time in 2003, includes in humans the following four proteins:
Interferon lambda-1 (IFN-$\lambda$1) or interleukin 29 (IL-29),
Interferon lambda-2 (IFN-$\lambda$2) or interleukin 28A (IL-28A),
Interferon lambda-3 (IFN-$\lambda$3) or interleukin 28B (IL-28B),
Interferon lambda-4 (IFN-$\lambda$4).

In mice, only two proteins belonging to this interferon III family have been identified to date (IFN-$\lambda$2/IL-28A and IFN-$\lambda$3/IL-28B).

These type III interferons mediate their effects via their common IFN-$\lambda$R1 receptor, also known as IL-28RA. A heterocomplex is formed between this receptor and the IL-10R2 receptor to bind IFN-$\lambda$ monomers (see Donnelly & Kotenko, 2010, for review).

In the context of the present invention, "gene encoding type III interferon" means one of the following genes, or their homologues:
The gene encoding IFN-$\lambda$1,
The gene encoding IFN-$\lambda$2,
The gene encoding IFN-$\lambda$3, and
The gene encoding IFN-$\lambda$4,
as described in the publications by Kotenko et al., 2003 and O'Brien et al., 2014.

It is understood that the genes cited above are human genes, but that if diltiazem is used in a different animal species, the genes encoding the type III interferons whose expression is activated by diltiazem will be at least one of the homologous genes of the species in question.

Induction of Expression of Major ISG

Example 1 of the present application demonstrates that diltiazem induces the expression of several so-called "interferon-stimulated" genes (ISGs), and in particular "immunity" genes, following apical or basolateral treatment.

Notably, diltiazem induces the expression of ISGs well described in the literature such as IF144L, IFIT2 OAS1, IRF7, MX1 or IFITM1.

Infections by Pathogenic Microorganisms of the Epithelia of the Respiratory and/or Intestinal Tracts The IFN-$\lambda$R1 receptor is exclusively expressed by epithelial-type cells, thus limiting the effects of type III interferons to epithelia.

In infections by external pathogens, the epithelia of the respiratory and intestinal tracts are the first organs affected, due to their direct contact, respectively, with the aspirated air and the ingested water and food.

Thus, the present invention relates in particular to diltiazem for use as an agent for activating the expression of at least one gene encoding a type III interferon, in the prevention and/or treatment of infections by at least one pathogenic microorganism of the epithelia of the respiratory and/or intestinal tracts.

The expression "infection by at least one pathogenic microorganism of the epithelia of the respiratory and/or intestinal tracts" should be understood as being an infection generated by the presence of at least one pathogenic microorganism, this microorganism having infected the individual or animal or being likely to infect the individual or animal.

It is indeed understood that the present invention relates to both the prevention and/or treatment of infections affecting humans (also referred to as "individuals"), as well as infections affecting animals, in particular livestock.

The term "prevention" refers to preventing, or at least decreasing the likelihood of, an infection in a human or animal organism by at least one pathogenic microorganism. Under the action of the type III interferons produced, the tissues of the organism and in particular the epithelia become more resistant and are better able to avoid and/or limit infection by said microorganism.

According to a particular implementation of the invention, diltiazem is used as an agent for activating the expression of at least one gene encoding a type III interferon, in the prevention of infections by at least one pathogenic microorganism of the epithelia of the respiratory and/or intestinal tracts.

The term "treatment" refers to fighting infection by at least one pathogenic microorganism in a human or animal organism. Through the administration of diltiazem, the rate of viral, bacterial, fungal or parasitic infection in the body will gradually decrease or even disappear completely. The term "treatment" also refers to reducing the symptoms associated with the infection (fever, fatigue, etc.) and/or to preventing/reducing the risk of complications, especially superinfection.

According to a particular implementation of the invention, diltiazem is used as an agent for activating the expression of at least one gene encoding a type III interferon, in the treatment of infections by at least one pathogenic microorganism of the epithelia of the respiratory and/or intestinal tracts.

According to a preferred aspect, the present invention relates to diltiazem for use as an agent for activating the expression of at least one gene encoding a type III interferon, in the prevention and/or treatment of infections by at least one pathogenic microorganism of the epithelia of the respiratory and/or intestinal tracts, characterized in that said at least one gene is selected from the gene encoding interleukin 29, the gene encoding interleukin 28A and the gene encoding interleukin 28B.

According to a particular implementation, diltiazem is used as an agent for activating the expression of the three genes encoding interleukin 29, interleukin 28A and interleukin 28B.

Pathogenic Microorganisms

In the context of the invention, the expression "pathogenic microorganisms" means any microorganism capable of creating a disease in other organisms, such as humans or animals. This expression includes in particular viruses, bacteria, fungi, protozoa, worms, and other pathogenic unicellular microorganisms.

Preferably, the "pathogenic microorganism" is a microorganism sensitive to the cellular response of the "interferon III" type, i.e. a microorganism whose cellular infection will be prevented or inhibited, totally or partially, by the expression and secretion of type III interferon proteins.

According to one aspect of the invention, the pathogenic microorganism is a microorganism that specifically infects the epithelia of the respiratory tract.

According to another aspect of the invention, the pathogenic microorganism is a microorganism that specifically infects the epithelia of the intestinal tract.

According to yet another aspect of the invention, the pathogenic microorganism is a microorganism capable of infecting all types of epithelia, particularly those of the respiratory and intestinal tracts.

According to a first aspect of the invention, the infection is a viral infection, i.e. the pathogenic microorganism of the epithelia of the respiratory and/or intestinal tracts is a virus.

Proteins belonging to the family of type III interferons are essential players in the antiviral response of the target epithelia of viruses. Thus, an agent that activates the expression of the genes encoding said type III interferon proteins stimulates and optimizes the antiviral response of infected epithelia.

According to this aspect, the invention relates to diltiazem for use as an agent for activating the expression of at least one gene encoding a type III interferon, in the prevention and/or treatment of infections by at least one virus infecting the epithelia of the respiratory and/or intestinal tracts.

In the context of the invention, the term "virus" includes any type of virus, but more particularly viruses infecting vertebrate eukaryotic organisms. These can be DNA or RNA viruses. In the context of the present invention, it refers more particularly here to viruses infecting organisms via the epithelia of the respiratory and/or intestinal tracts.

According to a particular aspect of the invention, the infection is not an influenza virus infection.

The therapeutic use of diltiazem to treat influenza virus infections has already been proposed in documents WO 2011/126071 and WO 2016/146836. However, diltiazem is used in the prior art for its action on calcium channels, and not for its action in activating the expression of genes encoding type III interferons.

According to a particular aspect of the invention, the pathogenic microorganism is a group I virus having a double-stranded DNA genome. This group of viruses includes, in particular, viruses of the order Herpes, those of the family Papillomaviridae, as well as Polyomaviridae and Poxviridae.

According to a particular aspect of the invention, the pathogenic microorganism is a group II virus having a single-stranded DNA genome, including in particular viruses of the family Parvoviridae.

According to one aspect of the invention, the pathogenic microorganism is a group III virus having a double-stranded RNA genome, including in particular viruses of the family Reoviridae, such as rotaviruses.

According to one aspect of the invention, the pathogenic microorganism is a group IV virus having a positive polarity single-stranded RNA genome. This group includes in particular:

viruses of the order Nidovirales, such as those of the family Coronaviridae;

viruses of the family Caliciviridae, including Norwalk virus;

viruses of the family Flaviviridae, including in particular yellow fever virus, West Nile virus, hepatitis C virus and dengue virus;

viruses of the family Picornaviridae, including polioviruses, rhinoviruses, and hepatitis A virus;

viruses of the family Togaviridae, including Rubella virus, Ross River virus, Sindbis virus and Chikungunya virus.

According to one aspect of the invention, the pathogenic microorganism is a group V virus having a single-stranded, negative polarity RNA (ssRNA) genome. This group includes in particular viruses of the order Mononegavirales, such as:

viruses of the family Bornaviridae, including the Bornaviridae, viruses of the family Filoviridae, including Ebola virus and Marburg virus, viruses of the family Paramyxoviridae, including measles virus, mumps virus and Henipavirus, viruses of the family Rhabdoviridae, including rabies virus, viruses of the family Arenaviridae, including Lassa fever virus, viruses of the family Bunyaviridae, including Hantaviruses and the Congo-Crimean Fever virus, viruses of the family Orthomyxoviridae.

According to a particular aspect of the invention, the pathogenic microorganism is a virus selected from human respiratory syncytial virus (hRSV), parainfluenza viruses (hPIV), human metapneumovirus (hMPV), Nipah virus, novoviruses, Swine fever virus, adenoviruses, coronaviruses, Zika virus, yellow fever virus, rheoviruses, rotaviruses, Dengue virus, and West Nile virus.

More particularly, the pathogenic microorganism is a virus selected from human respiratory syncytial virus (hRSV), parainfluenza viruses (hPIV) and human metapneumovirus (hMPV).

According to a particular implementation, the invention relates to diltiazem for use as an agent for activating the expression of at least one gene encoding a type III interferon, in the prevention and/or treatment of human respiratory syncytial virus (hRSV) infections.

More particularly, the invention relates to diltiazem for use in the prevention and/or treatment of human respiratory syncytial virus (hRSV) infections.

According to another implementation, the invention relates to diltiazem for use as an agent for activating the expression of at least one gene encoding a type III interferon, in the prevention and/or treatment of human parainfluenza virus (hPIV) infections.

More particularly, the invention relates to diltiazem for use in the prevention and/or treatment of human parainfluenza virus (hPIV) infections.

According to a particular implementation, the invention relates to diltiazem for use as an agent for activating the expression of at least one gene encoding a type III interferon, in the prevention and/or treatment of human metapneumovirus (hMPV) infections.

More particularly, the invention relates to diltiazem for use in the prevention and/or treatment of human metapneumovirus (hMPV) infections.

According to a second aspect of the invention, the infection is a non-viral infection. In particular, the pathogenic microorganism can be selected from a bacterium, a fungus and a parasite.

According to a particular aspect of the invention, the pathogenic microorganism is a bacterium.

Among pathogenic bacteria, particular mention may be made of bacteria of the following species: *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae*

Mention may also be made of the bacteria specific to intestinal infections such as *Campylobacter* spp., *Salmonella* spp., *Yersinia enterocolitica, Vibrio cholerae, Escherichia coli, Staphylococcus aureus, Bacillus cereus*, and *Clostridium difficile.*

According to a particular aspect of the invention, the pathogenic microorganism is not a bacterium of the genus *Chlamydiae.*

According to a particular aspect of the invention, the pathogenic microorganism is a bacterium selected from the following bacterial species: *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella Typhimurium, Streptococcus pneumoniae, Haemophilus influenzae, Campylobacter* spp., *Salmonella* spp., *Shigella* spp., *Yersinia enterocolitica, Vibrio cholerae, Escherichia coli, Staphylococcus aureus, Bacillus cereus*, and *Clostridium difficile.*

According to a particular implementation, the pathogenic microorganism is a bacterium of the species *Pseudomonas aeruginosa.*

According to a particular implementation, the invention relates to diltiazem for use as an agent for activating the expression of at least one gene encoding a type III interferon, in the prevention and/or treatment of *Pseudomonas aeruginosa* infections.

More particularly, the invention relates to diltiazem for use in the prevention and/or treatment of *Pseudomonas aeruginosa* infections.

According to a particular aspect of the invention, the pathogenic microorganism is a fungus.

Among pathogenic fungi, particular mention may be made of *Aspergillus fumigatus, Candida albicans, Pneumocystis jiroveci, Fusarium solari.*

According to another implementation, the invention relates to diltiazem for use as an agent for activating the expression of at least one gene encoding a type III interferon, in the prevention and/or treatment of infections by a pathogenic microorganism selected from the following group: *Pseudomonas aeruginosa*, human respiratory syncytial virus (hRSV), parainfluenza viruses (hPIV) and human metapneumovirus (hMPV).

More particularly, the invention relates to diltiazem for use in the prevention and/or treatment of infections by a pathogenic microorganism selected from the following group: *Pseudomonas aeruginosa*, human respiratory syncytial virus (hRSV), parainfluenza viruses (hPIV) and human metapneumovirus (hMPV).

The expression "at least one pathogenic microorganism" means that one or more pathogenic microorganisms are present in the infected organism, thus generating an immune response from the organism.

In particular, the organism may have been infected with both a virus and a bacterium, which is referred to as co-infection of the organism.

According to a particular aspect, the invention relates to diltiazem for use as described above, characterized in that the infection is a co-infection by at least one virus and at least one bacterium.

Advantageously, diltiazem is then used for the concomitant treatment of a viral infection and a bacterial infection, which limits the number of active compounds administered to an individual or an animal suffering from this co-infection.

More specifically, this co-infection may be linked to the presence in infected epithelia of a combination of pathogenic microorganisms selected from the following:

A human respiratory syncytial virus (hRSV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae.* a parainfluenza virus (hPIV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae,* a human metapneumovirus (hMPV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae,* a Nipah virus and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae,* a novovirus and at least one bacterium of a species selected from *Campylobacter* spp., *Salmonella* spp., *Escherichia coli, Staphylococcus aureus, Bacillus cereus*, and *Clostridium difficile,* a coronavirus and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae,*

Swine fever virus and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae,* an adenovirus and at least one bacterium of a species selected from *Enterococcus faecalis, Borrelia burgdorferi, Listeria monocytogenes, Mycobacterium tuberculosis, Pseudomonas aeruginosa, Staphylococcus* aureus, *Staphylococcus epidermidis*, *Salmonella typhimurium*, *Streptococcus pneumoniae* and *Haemophilus influenzae*, Zika virus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*, yellow fever virus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*, a reovirus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*, a rotavirus and at least one bacterium of a species selected from *Campylobacter* spp., *Salmonella* spp., *Escherichia coli*, *Staphylococcus aureus*, *Bacillus cereus*, and *Clostridium difficile*, Dengue virus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*, West Nile virus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*, and An influenza virus and at least one bacterium of a species selected from *Enterococcus faecalis*, *Borrelia burgdorferi*, *Listeria monocytogenes*, *Mycobacterium tuberculosis*, *Pseudomonas aeruginosa*, *Staphylococcus aureus*, *Staphylococcus epidermidis*, *Salmonella typhimurium*, *Streptococcus pneumoniae* and *Haemophilus influenzae*.

According to a particular implementation of the invention, diltiazem as an agent for activating the expression of at least one gene encoding a type III interferon will be used for both:
  i) Treating viral infection of the epithelia of the respiratory and/or intestinal tracts; and
  ii) Preventing co-infection by at least one other pathogenic microorganism of the epithelia of the respiratory and/or intestinal tracts, such as bacterial superinfection.

According to another particular implementation of the invention, diltiazem as an agent for activating the expression of at least one gene encoding a type III interferon will be used for both:
  i) Treating bacterial infection of the epithelia of the respiratory and/or intestinal tracts; and
  ii) Preventing co-infection by at least one other pathogenic microorganism of the epithelia of the respiratory and/or intestinal tracts, such as viral superinfection.

According to another particular implementation of the invention, diltiazem as an agent for activating the expression of at least one gene encoding a type III interferon will be used for both:
  i) Treating viral infection of the epithelia of the respiratory and/or intestinal tracts; and
  ii) Treat co-infection with at least one other pathogenic microorganism of the epithelia of the respiratory and/or intestinal tracts, such as bacterial superinfection.

Therapeutic Combinations

The present invention also relates to diltiazem for therapeutic use as previously presented, characterized in that it is used in combination with at least one other active agent, i.e. with one or more active agents.

Preferably, this other active agent is a therapeutic compound having a beneficial action on a human or animal organism, with the goal of preventing or treating a pathology.

In particular, this other active agent will be selected from an antiviral compound, an antibacterial compound, an antiparasitic compound, an antifungal compound, and a preventive or therapeutic vaccine.

Preferably, this other active agent is selected from an antiviral compound and an antibacterial compound.

In the context of the invention, "antiviral compound" means a compound having either a direct inhibitory action on at least one virus (for example, inhibiting its replication) or an action on a target cell of the virus (for example, inducing a cellular state unfavorable to a viral infection, thereby preventing the viral infection).

Antiviral agents are classified into different categories according to their mode of action. Particular mention may be made of:
  nucleotide analogues, which interfere with or stop DNA or RNA synthesis; as well as inhibitors of enzymes involved in DNA or RNA synthesis (helicase, replicase);
  compounds that inhibit the maturation stages of the virus during its replication cycle;
  compounds that interfere with binding to the cell membrane, or with entry of viruses into host cells (fusion or entry inhibitors);
  agents that prevent the virus from expressing itself within the host cell after its entry, by blocking its disassembly within the cell;
  agents that restrict the spread of viruses to other cells.

In particular, the antiviral agent(s) is (are) selected from:
  i) viral agents having direct inhibitory action on viruses, such as for example ribavirin and favipiravir;
  ii) active agents inducing cellular states that are globally unfavorable to viral infection; and
  iii) compounds selected from the following compounds:
    substituted 2-deoxyuridine analogs;
    nucleoside analogues;
    pyrophosphate analogs;
    protease inhibitors;
    inhibitors of virus penetration into cells, such as arbidol;
    monoclonal antibodies, such as palivizumab, directed against an epitope of the A antigenic site of the respiratory syncytial virus (RSV) fusion protein; and antisense oligonucleotides with virus-inhibitory action.

In the context of the invention, "antibacterial compound" means a compound having antibacterial activity, i.e. inhibiting the replication of bacteria (bacteriostatic compounds)

or destroying them (bactericidal compounds) or inhibiting their biosynthesis and/or secretion of toxic products. These are in particular antibiotics.

In particular, the antibacterial agent(s) is (are) selected from:
i) antibiotics, and particularly those of the macrolide family, especially roxithromycin;
ii) bacteriophages, natural predators of bacteria.

Such antiviral and antibacterial agents are commercially available, and their conditions of use are described in reference works such as Le Dictionnaire Vidal.

According to another aspect of the invention, the other active agent used in combination with diltiazem is an antifungal compound or an antiparasitic compound, in particular selected from systemic antifungal compounds (amphotericin B, azoles, echinocandins) and systemic antiparasitic compounds (for example antimalarial, antiamoebic, toxoplasmosis, leishmaniasis, pneumocytosis, antihelminthic drugs).

According to a particular implementation of the invention, the at least one other active agent is a vaccine.

In the context of the invention, "vaccine" means a compound or combination of compounds that specifically stimulates the immune system of a human or animal organism. In particular, a vaccine will include an antigen, i.e. a compound inducing a specific immune response in the organism, which will retain the memory of that response.

Such a vaccine could be a preventive vaccine, i.e., intended to stimulate a specific immune response before an organism is infected by a pathogenic microorganism.

Examples include, but are not limited to, different types of vaccines, classified according to the nature of the antigens from which they are prepared. The antigens traditionally used are the following: inactivated infectious agents, live attenuated agents, subunits of infectious agents, toxoids, viral vectors expressing antigens derived from pathogens, vectors carrying nucleic acids (DNA or RNA), and antibodies.

Such a vaccine may also be a therapeutic vaccine, i.e., intended to stimulate a specific immune response concomitantly with the infection of an organism by a pathogenic microorganism.

In all cases, it is understood that this vaccine may be administered before, during, or after treatment with diltiazem.

Finally, according to a particular aspect of the invention, all the active agents cited above may be used in combination with each other, for example combinations of the type:
diltiazem, antiviral compound and antibacterial compound,
diltiazem, antiviral compound and antiparasitic compound,
diltiazem, antibacterial compound and antifungal compound,
diltiazem and preventive vaccine; or
diltiazem and therapeutic vaccine,
may be administered concomitantly or sequentially to an individual or animal with an infection, by one or more pathogenic microorganisms, of the epithelia of the respiratory and/or intestinal tracts.

Pharmaceutical or Veterinary Composition

The present invention also relates to a pharmaceutical or veterinary composition comprising diltiazem as an agent for activating the expression of at least one gene encoding a type III interferon.

The present invention also relates to a pharmaceutical or veterinary composition comprising diltiazem as an agent for activating the expression of at least one gene encoding a type III interferon, for use in the prevention and/or treatment of infections by pathogenic microorganisms of the epithelia of the respiratory and/or intestinal tracts.

More precisely, this composition according to the invention will comprise diltiazem as well as a suitable pharmaceutical vehicle, and optionally another active agent.

The term "suitable pharmaceutical vehicle" refers to pharmaceutically acceptable vehicles or excipients, i.e. vehicles or excipients whose administration to an individual or animal is not accompanied by significant deleterious effects, and which are well known to the skilled person.

This composition according to the invention may be adapted for any type of administration and in particular for oral, sublingual, nasal and/or oral administration by inhalation, subcutaneous, intramuscular, intravenous, transdermal, ocular or rectal administration.

Suitable galenic forms of administration may for example be tablets, capsules, powders, granules, solutions or suspensions.

According to a particular aspect, the pharmaceutical or veterinary composition is characterized in that it is in a galenic form suitable for administration by inhalation, i.e. by the nasal and/or oral routes.

Inhalation refers to absorption through the respiratory tract. It is a method of absorbing therapeutic compounds in the form of gas, microdroplets or powder suspension.

Two types of administration by inhalation can be distinguished:
administration by insufflation when the compositions are in powder form, and
administration by nebulization when the compositions are in the form of aerosols (suspensions) or in the form of solutions, for example aqueous solutions, under pressure. The use of a nebulizer or a sprayer will then be recommended to administer the pharmaceutical or veterinary composition.

The suitable galenic form for administration of diltiazem by inhalation is selected from: powder, aqueous suspension of droplets, or solution under pressure.

According to one aspect of the invention, the pharmaceutical or veterinary composition comprises an effective amount of diltiazem, for use as an agent for activating the expression of at least one gene encoding a type III interferon, in the prevention and/or treatment of infections by at least one pathogenic microorganism of the epithelia of the respiratory and/or intestinal tracts.

Persons skilled in the art will be able, through their general knowledge, to easily identify the effective amount of diltiazem that should be administered to obtain an action on the expression of at least one gene encoding a type III interferon.

The present invention also relates to a combination product comprising:
diltiazem as an agent for activating the expression of at least one gene encoding a type III interferon, and
at least one other active agent selected from an antiviral compound, an antibacterial compound, and an agent for preventing infections by pathogenic microorganisms, for simultaneous, separate or sequential use to prevent and/or treat infection by pathogenic microorganisms of the epithelia of the respiratory and/or intestinal tracts.

The present invention also relates to a method for preventing and/or treating infection in an individual infected or susceptible to infection by at least one pathogenic microorganism of the epithelia of the respiratory and/or intestinal tracts, comprising the administration of diltiazem to this individual, to activate the expression of at least one gene encoding a type III interferon.

The present invention also relates to a method for preventing and/or treating infection in an individual infected or susceptible to infection with at least one pathogenic microorganism of the epithelia of the respiratory and/or intestinal tracts, comprising the administration of diltiazem to said individual, the diltiazem being used as an agent for activating the expression of at least one gene encoding a type III interferon.

The present invention also relates to a method for preventing and/or treating infection in an animal infected or susceptible to infection by at least one pathogenic microorganism of the epithelia of the respiratory and/or intestinal tracts, comprising the administration of diltiazem to this animal, to activate the expression of at least one gene encoding a type III interferon.

This administration of diltiazem will preferably be performed by inhalation.

EXAMPLES

It is understood that the examples presented in this section are in no way limiting, and that they only illustrate the invention as described above.

Example 1. Characterization by RNAseq and RT-qPCR of the Induction by Diltiazem of the Expression of Type III Interferon Genes A—Diltiazem Applied to the Basolateral Pole of Reconstituted Human Respiratory Epithelia (MucilAir® HAE, Epithelix)

Reconstituted human respiratory epithelia (MucilAir® HAE, Epithelix) maintained in culture at the air-liquid interface according to the instructions of the supplier Epithelix, were treated or not with diltiazem (90 µM) via their culture medium at their basolateral pole. The diltiazem treatment was repeated for 3 consecutive days (3 administrations in total).

Treated and untreated epithelia were then lysed with 150 µL of RLT buffer (Qiagen). Total RNA was extracted using the RNeasy Kit (Qiagen) according to the supplier's instructions. cDNA libraries were prepared from 200 ng of total RNA using the ScriptSeq™ Complete Gold Kit-Low Input (SCL6EP, Epicentre) according to the supplier's instructions. Each library was amplified, quantified and indexed with primers provided in the ScriptSeq™ Index PCR Primers Kit (RSBC10948, Epicentre) and sequenced. Sequencing was conducted on an Illumina HiSeq 2500 system with a minimum requirement of 40 million "reads" sequenced per sample.

The demultiplexing of the data and the conversion of the BCL files resulting from the sequencing into FASTQ files were carried out using Illumina's bcl2fastq tool, in its version 1.8.4. The FastQC software (http://www.bioinformatics.babraham.ac.uk/projects/fastqc) was used to perform the necessary quality controls on the raw data. "Trimming" was performed using the Trimmomatic tool, with a minimum quality threshold equal to Q30. A pseudo-alignment of the trimmed reads on the human genome (*Homo Sapiens*: GRCh38.p11) using the Kallisto software was performed, followed by a statistical analysis using the R 3.3.1 software and the EdgeR 3.14.0 package.

The differential in gene expression between epithelial cells treated with diltiazem and control epithelial cells was calculated using a linear model with a p-value correction by the Benjamini-Hochberg method.

Only genes displaying an expression differential greater than or equal to 2, and a corrected p-value less than 0.05, were considered in the rest of the analysis.

These genes were subjected to functional enrichment analyses using the DAVID 6.8 tool as well as association and interaction studies using the STRING tool.

Figure 1A:
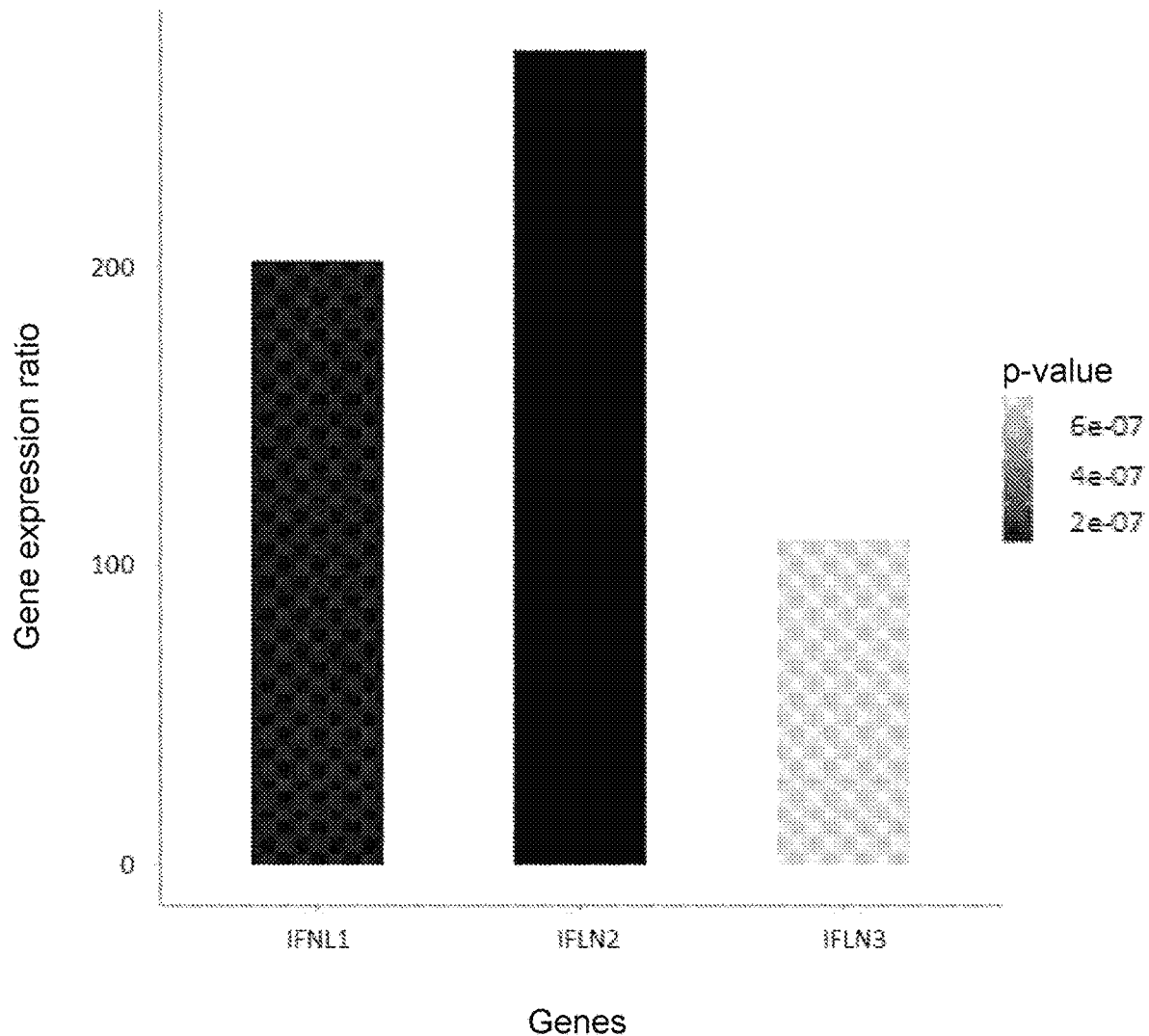
FIG. 1: Characterization of the induction of type III interferon gene expression by basolateral diltiazem treatment of the 3D model of reconstituted human respiratory epithelium of nasal origin (MucilAir® HAE, Epithelix).

FIG. 1A shows the expression ratios of the type III interferon IFN-λ1, IFN-λ2 and IFN-λ3 genes observed between human respiratory epithelia treated with diltiazem and untreated control human respiratory epithelia.

Figure 1B:
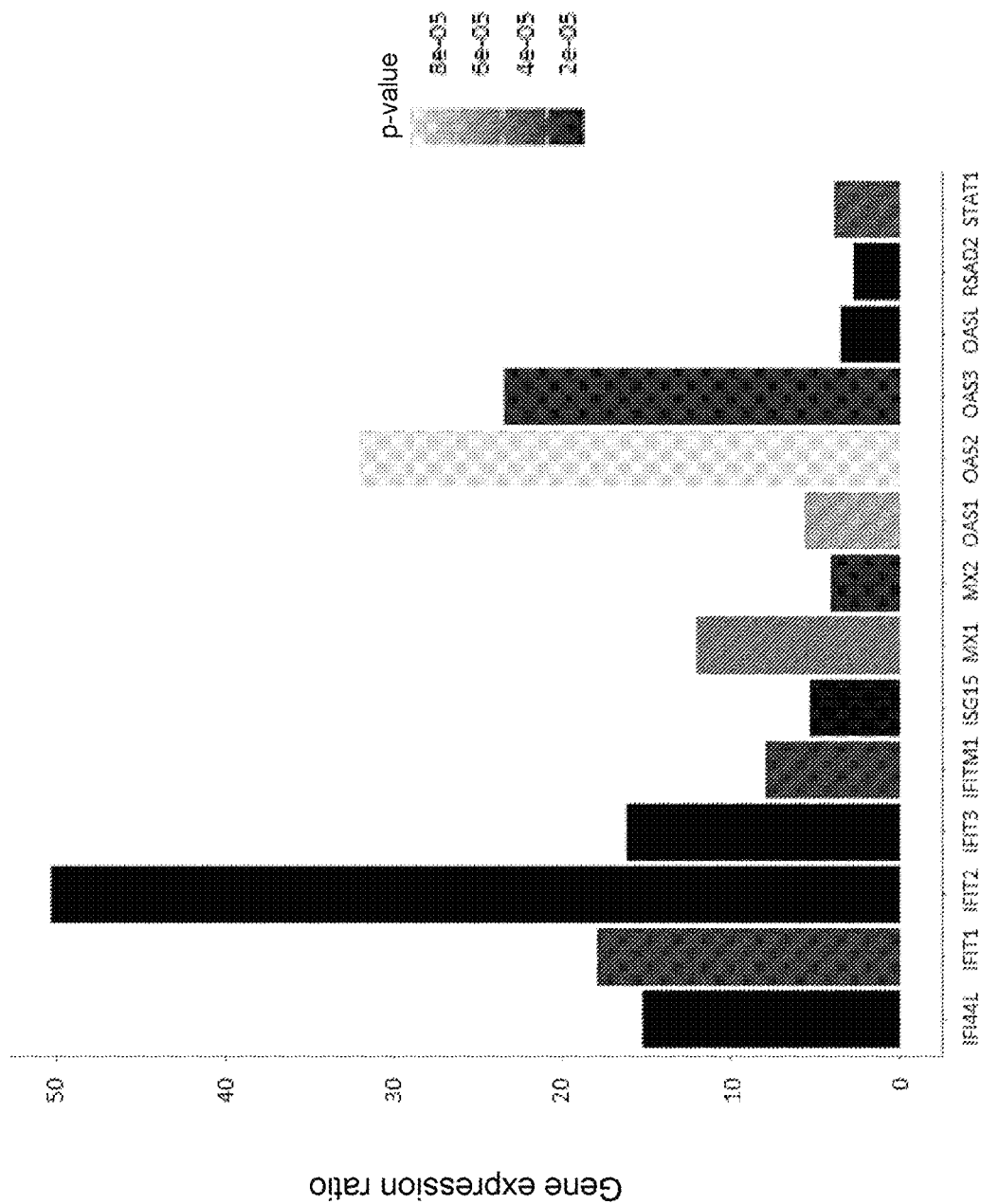

FIG. 1B shows the expression ratios of type III interferon response genes such as IF144L, IFIT1, IFIT2, IFIT3, IFITM1, ISG15, MX1, MX2, OAS1, OAS2, OAS3, OASL, RSAD2 and STAT1 observed between diltiazem-treated human respiratory epithelia and untreated control human respiratory epithelia.

It is clear that treatment with diltiazem of reconstituted human respiratory epithelia, for 3 days, significantly alters the level of expression of the genes encoding the type III interferons IFN-λ1, IFN-λ2 and IFN-λ3, increasing it significantly (from 100 to more than 200 times compared with untreated control epithelia). In addition, this treatment also significantly stimulates the expression of type III interferon response genes such as IF144L, IFIT1, IFIT2, IFIT3, IFITM1, ISG15, MX1, MX2, OAS1, OAS2, OAS3, OASL, RSAD2 and STAT1.

B—Diltiazem Applied to the Apical Pole of Reconstituted Human Respiratory Epithelia (Mucilair® Hae, Epithelix)

We have shown above that diltiazem treatment of epithelia via the basolateral medium (mimicking per os delivery in a mouse model and in humans) induces expression of the IFN III pathway.

The objective of this experiment was to confirm that this induction by diltiazem is also effective when the molecule is administered via the apical pole of the epithelia, mimicking the mode of delivery via the intranasal route in vivo.

Figure 1C:
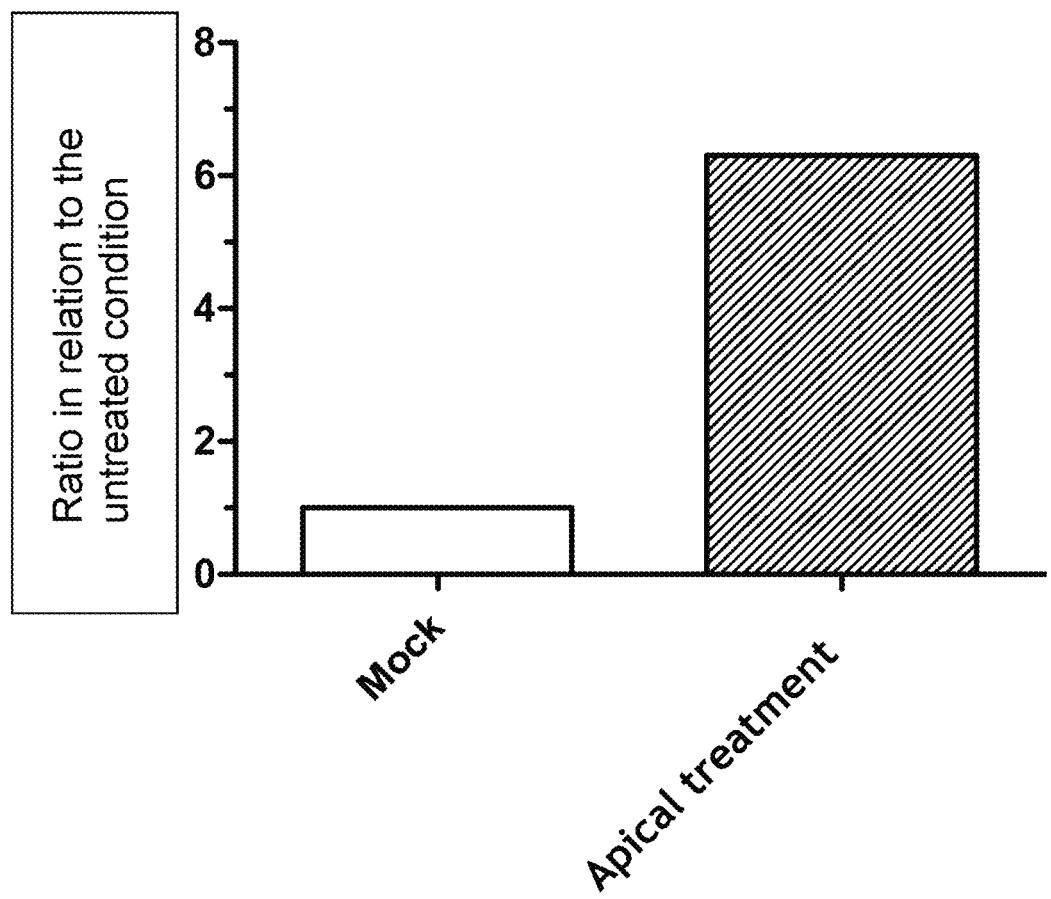

FIG. 1C presents the results obtained 24 hours after apical pole treatment of reconstituted human epithelial models (MucilAir® HAE, Epithelix) with diltiazem, on the expression of the endogenous IFNL1 (interferon lambda I) gene, compared with the endogenous expression of untreated epithelia (control). The measurement was performed by RT-qPCR.

The results obtained indicate that the treatment of human respiratory epithelia reconstituted by diltiazem via their apical pole induces a significant overexpression of the IFNL1 gene, with an expression ratio higher than 6:1 compared with control (untreated) epithelia.

These results allow us to confirm that diltiazem administered via the apical pole of reconstituted human respiratory epithelia (this route of administration mimics in vitro an intranasal in vivo administration), also activates the IFN III pathway, as well as treatment via the basolateral pole, which mimics the per os in vivo administration.

Example 2. Confirmation by Rt-qPCR of the Induction by Diltiazem of the Expression of 8 Genes Associated with the "Type III Interferon" Response Reconstituted human respiratory epithelia (MucilAir® HAE, Epithelix) were maintained in culture at the air-liquid interface according to the instructions of the supplier Epithelix and were treated or not with diltiazem (90 µM) via their culture medium at their basolateral pole. The diltiazem treatment was repeated for 3 consecutive days (3 administrations in total).

Treated and untreated epithelia were then lysed with 150 µL of RLT buffer (Qiagen). Total RNA was extracted using the RNeasy Kit (Qiagen) according to the supplier's instructions. After a reverse transcription step, a real-time quantitative PCR reaction was performed using the StepOnePlus™ Real-Time PCR System (Applied Biosystems) in a 96-well plate.

The quantitative PCR primers (GAPDH: Hs02758991_g1, IFNL1: Hs00601677_g1, IFNL2: Hs00820125_g1, IFIT1: Hs01675197_m1, IFIT2: Hs00533665_m1, IFIT3: Hs00382744_m1, IF127: Hs01086373_g1, IF144L: Hs00915292_m1, IFITM1: Hs01652522_g1) and probes (TaqMan gene expression assays) were provided by Thermo Fisher Scientific.

Each sample was analyzed in triplicate and the cycle threshold (Ct) was normalized to the GAPDH reference.

The expression ratios of the IFIT1, IFIT2, IFIT3, IF127, IFN-1, IFN-2, IF144L and IFITM1 genes between cells treated with diltiazem and untreated cells were determined by the 2ΔΔCt method (Livak and Schmittgen, 2001).

FIG. 2 presents the results obtained: after treatment with diltiazem, reconstituted epithelia show a significant increase in the expression of the IFIT1, IFIT2, IFIT3, IF127, IFN-$\lambda$1, IFN-$\lambda$2, IF144L and IFITM1 genes compared with untreated epithelia.

Example 3. ELISA Measurement of Diltiazem-Stimulated Secretion of Type III Interferon Lambda 1 (IL-29)

Reconstituted human respiratory epithelia (MucilAir® HAE, Epithelix) were maintained in culture at the air-liquid interface according to the instructions of the supplier Epithelix and were treated or not with diltiazem (90 µM) via their culture medium at their basolateral pole. The diltiazem treatment was repeated for 3 consecutive days (3 administrations in total).

Secretion levels (pg/mL) of interferon lambda 1 (IL-29) at the apical and basolateral poles of human respiratory epithelia treated and untreated with diltiazem were measured by ELISA after 72 h of treatment according to the supplier's instructions (#3570-1H, Mabtech, Stockholm, Sweden).

FIG. 3 presents the results obtained: IFN-$\lambda$1 (IL-29) secretion is very sharply increased at the apical pole following treatment with diltiazem via the epithelial culture medium; a significant, but less marked, increase is also observed at the basolateral pole of treated epithelia.

Example 4. Diltiazem Treatment Significantly Reduces the Replication of the Respiratory Syncytial Virus A—In Vitro Results Reconstituted human respiratory epithelia (MucilAir® HAE, Epithelix) were maintained in culture at the air-liquid interface according to the instructions of the supplier Epithelix and were infected with respiratory syncytial virus (Long strain, ATCC VR-26) at a multiplicity of infection (MOI) 1, then treated or not with diltiazem (90 µM) via their culture medium at their basolateral pole. Diltiazem treatment was performed at 5 hours post-infection and then repeated for 3 consecutive days (4 administrations in total).

At 6 days post-infection, samples at the apical pole of treated and untreated infected epithelia, as well as the epithelia themselves, were lysed with 150 µL of RLT buffer (Qiagen). The process of the experiment is schematically represented in FIG. 4A.

Figures 4A, 4B, 4C:
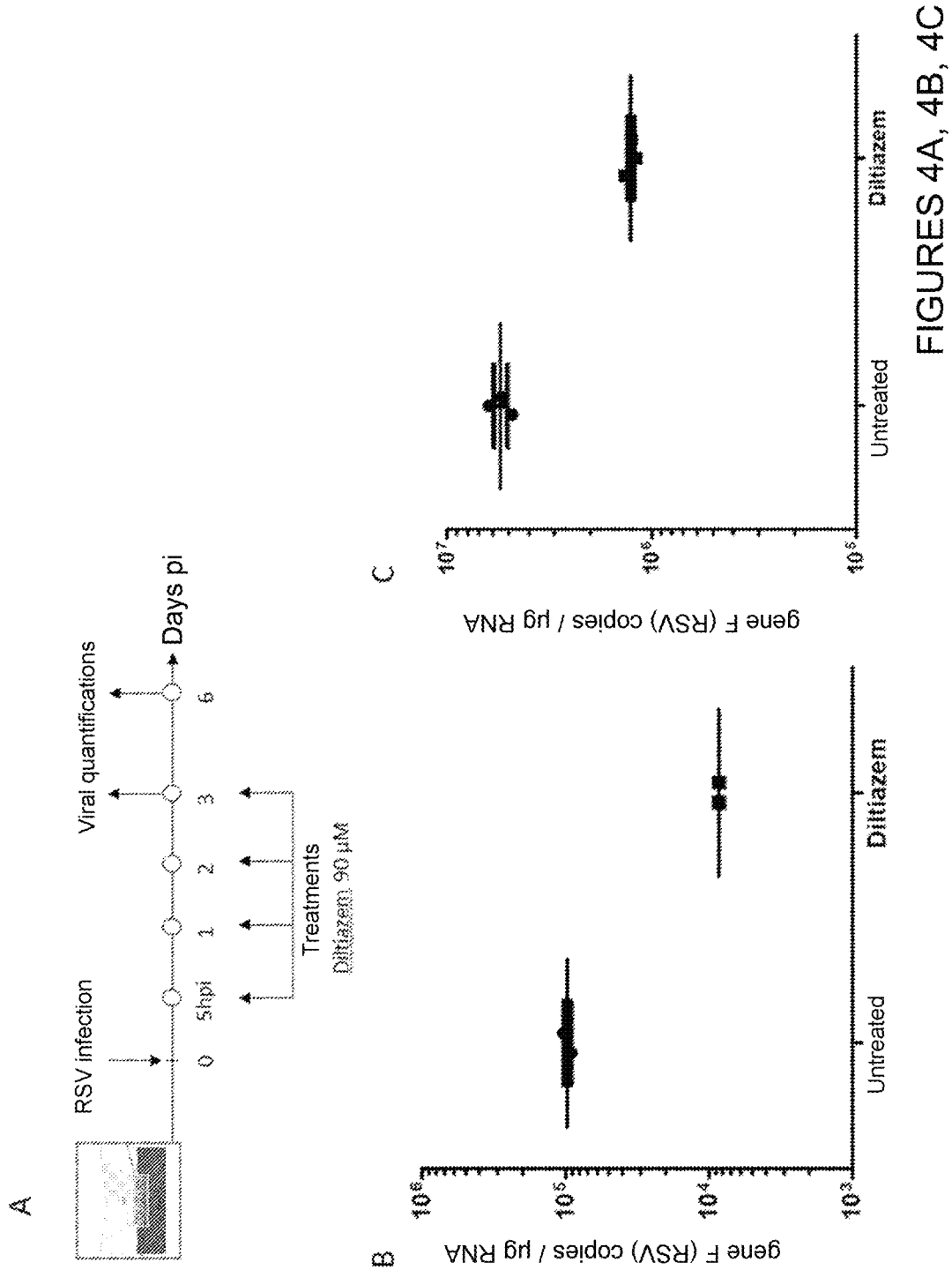

Total RNA was extracted using the RNeasy Kit (Qiagen), according to the supplier's instructions, for quantification of viral genome copy number (F gene) by RT-qPCR at the apical pole, i.e. in the supernatant (FIG. 4B), as well as in the epithelia (FIG. 4C).

FIGS. 4B and 4C show that when reconstituted human respiratory epithelia were treated post-infection with diltiazem (90 µM) via their basolateral pole, the amount of viral genome is much lower in both the culture supernatant (FIG. 4B) and the epithelium (FIG. 4C) compared with untreated epithelia. Diltiazem therefore has a significant antiviral effect against respiratory syncytial virus in reconstituted human respiratory epithelia models.

B—In Vivo Results

Diltiazem (per os) treatment reduces the replication of respiratory syncytial virus (RSV) in a BALB/c mouse model after challenge infection.

Figure 4D:
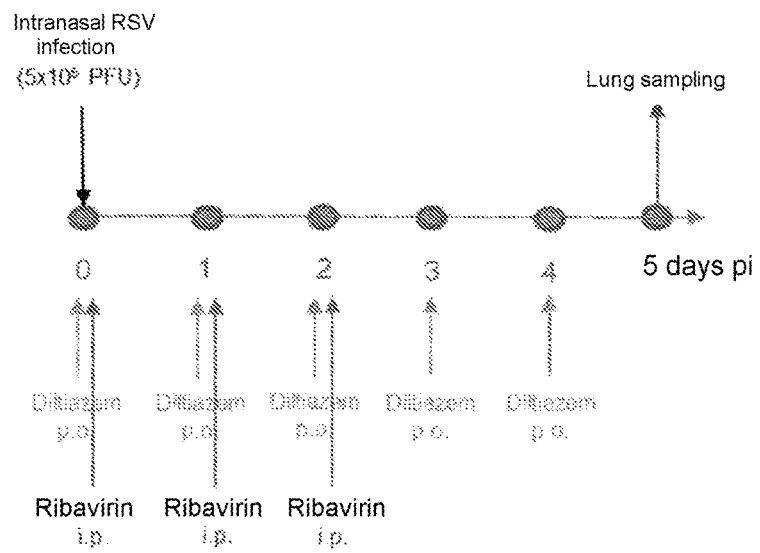

FIG. 4D schematically represents the chronology of infection and treatment of the mice:

BALB/c mice were randomized into 3 groups of 5 individuals and then infected intranasally with 50 µL of a viral suspension containing $5\times10^5$ PFU of RSV (Day 0). Six hours before infection, the mice were treated with either 40 mg/kg intraperitoneal ribavirin (RSV RIB) or 50 mg/kg diltiazem peros (RSV DIL), or PBS (RSV PBS) as negative control.

The same treatments were repeated every 24 h, with a total of 3 treatments for ribavirin and 5 treatments for diltiazem or PBS.

On day 5 post-infection (D5, corresponding to the peak of viral replication), the mice in each group were euthanized and their lungs were aseptically recovered to measure their pulmonary viral titers by RTqPCR (F gene).

Figure 4E:
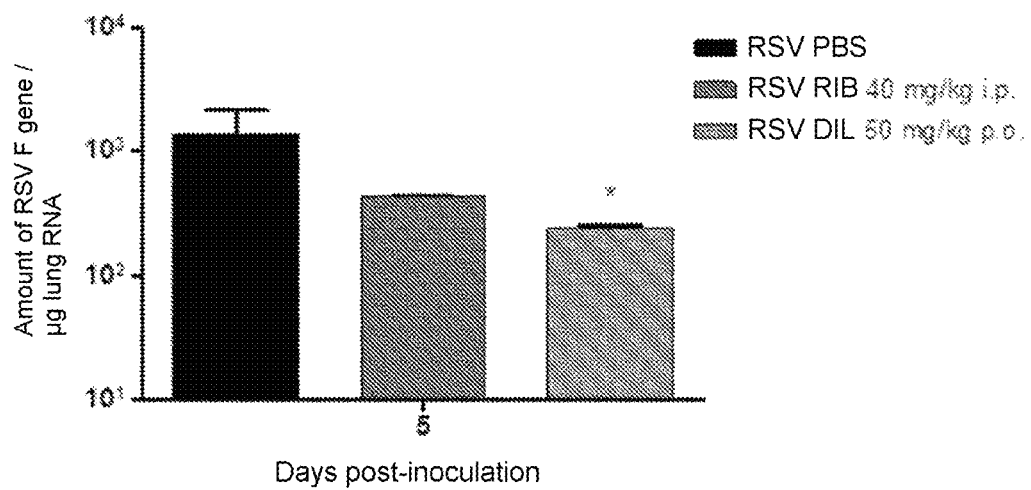

RT-qPCR quantification of the RSV viral genome copy number (quantifying the copies of the F gene) relative to the total amount of RNA extracted from the lungs at 5 days post-infection was performed, and the results are presented in FIG. 4E.

Animals treated with diltiazem (RSV DIL) had significantly reduced pulmonary viral titers compared with animals in the control group (RSV PBS) and animals in the ribavirin-treated group (RSV RIB).

The following statistical tests were used: One-way ANOVA with Bonferroni post-test to compare each virus to the mock condition (PBS treatment). *$p<0.05$.

Diltiazem therefore has a significant antiviral effect against the respiratory syncytial virus in a mouse model in vivo.

Example 5. Diltiazem Treatment Significantly Reduces the Replication of Parainfluenza Virus Type 3

Figure 5A:
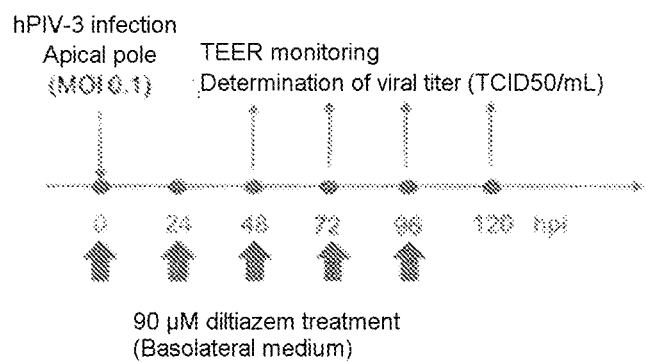

The experimental design is shown in FIG. 5A.

Reconstituted human respiratory epithelia were infected with human parainfluenza virus type 3 (strain C243 ATCC VR-93) at an MOI of 0.1, and treatment of the basolateral medium with 90 µM diltiazem was started 2 hours post-infection and continued daily for 4 consecutive days. Transepithelial electrical resistance (TEER), which reflects the integrity of the epithelium, was measured once daily from 48 h post-infection to 120 hours post-infection.

Apical infectious viral titers (TCID50/mL) were determined in LLC-MK2 cells from washings collected starting 48 h post-infection (hpi), and up to 120 hpi, as shown in FIG. 5A.

Figure 5B:
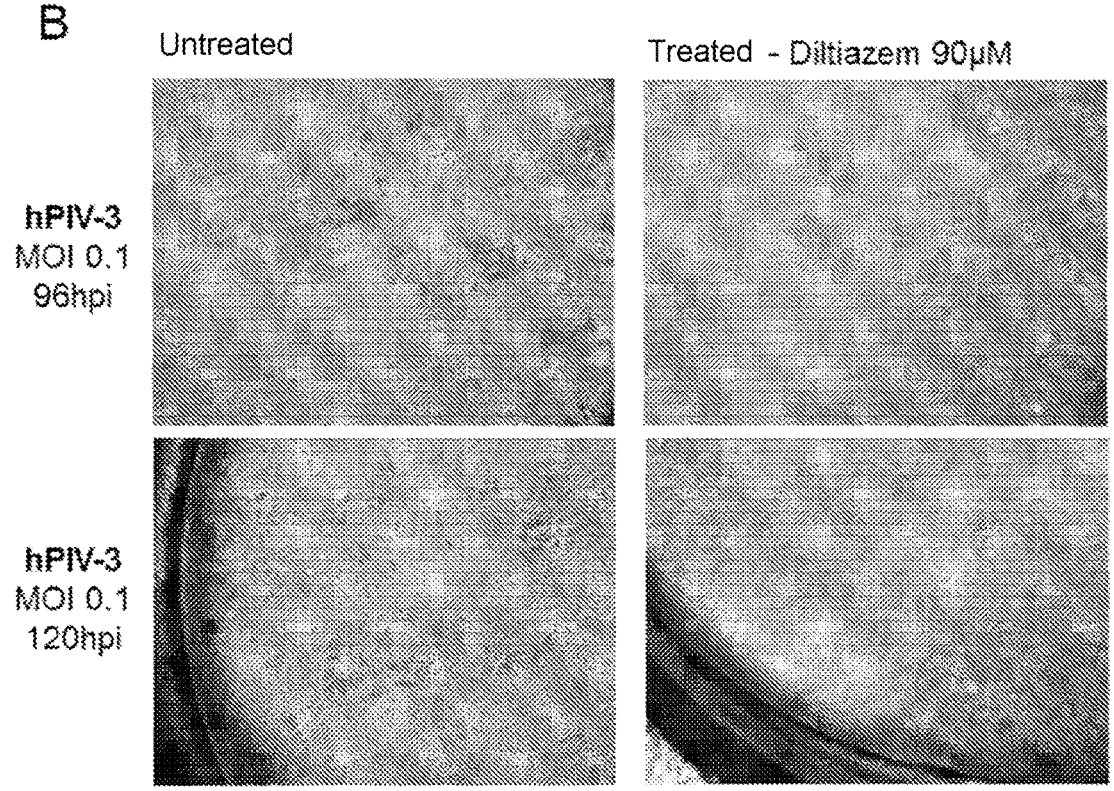

FIG. 5B shows the results obtained after the following experiment: at 96 and 120 hpi, untreated reconstituted human respiratory epithelia (images at left) and diltiazem-treated human respiratory epithelia (images at right) were observed under the microscope. The cytopathic effects induced by hPIV-3 were greater and easily visible microscopically in untreated reconstituted human respiratory epithelia, unlike those treated with diltiazem.

Figures 5C, 5D:
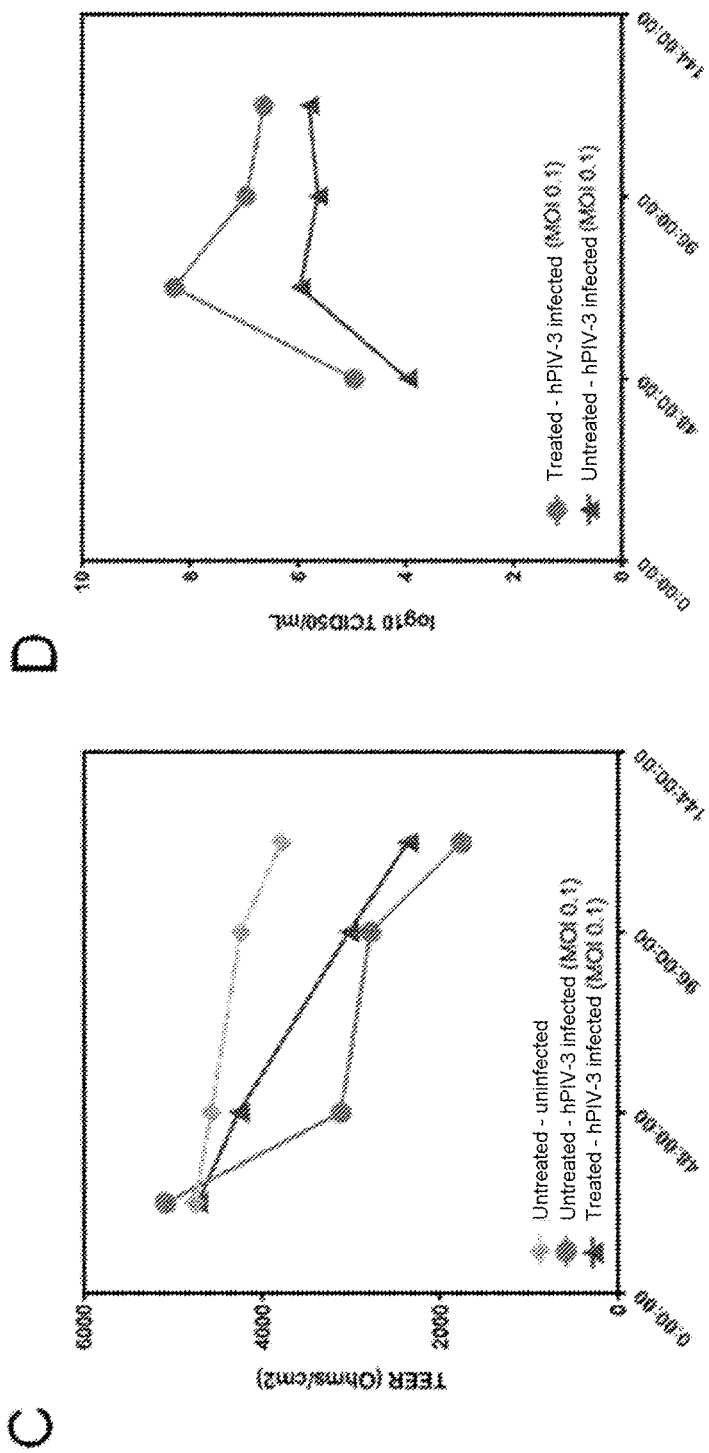

FIG. 5C shows TEER values as a function of time post-infection, measured on reconstituted human respiratory epithelia:
  untreated, uninfected;
  untreated, infected with hPIV-3; and
  treated with diltiazem, infected with hPIV-3.

These results demonstrate that absent treatment, TEER values decrease significantly, from 24 hpi, unlike the values measured on reconstituted human respiratory epithelia treated with diltiazem, whose integrity appears to be more preserved.

FIG. 5D shows the measured viral titers (in LLC-MK2 (TCID50/mL) over time (from 48 to 120 hpi) at the apical surface of reconstituted human respiratory epithelia treated and untreated with diltiazem.

Absent treatment, infectious viral titers measured at the apical surface of reconstituted human respiratory epithelia peaked at 72 h post-infection at a value of $10^8$ TCID50/mL) and at 96 h post-infection at a value of $10^7$ TCID50/mL, unlike reconstituted human respiratory epithelia treated with diltiazem, which show significantly lower values at 72 h post-infection ($10^6$TCID50/mL) and at 96 h post-infection ($10^5$TCID50/mL).

On the whole, these results indicate that diltiazem treatment reduces viral replication of hPIV-3 in the infected reconstituted human respiratory epithelium model.

Example 6. Diltiazem Treatment Significantly Reduces the Multiplication of the Bacterium Pseudomonas aeruginosa The experimental design is shown in FIG. 6A.

Reconstituted human respiratory epithelia were pre-treated 24 hours prior to infection with 90 µM diltiazem in basolateral medium or alternatively with 10 µL of 90 µM diltiazem at the apical surface, then infected with Pseudomonas aeruginosa (PAK strain) at an MOI of 1 and re-treated with diltiazem 2 hours after infection.

Figures 6A, 6B, 6C:
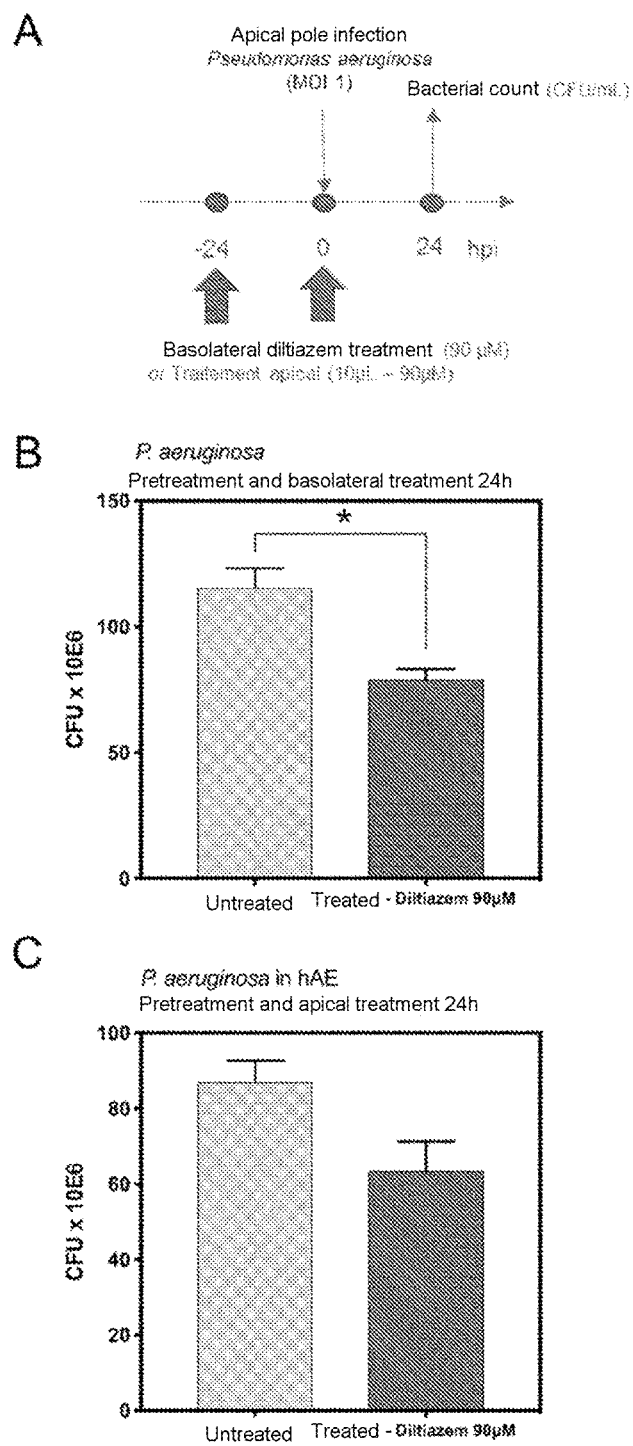

The results are presented in FIG. 6B (for basolateral treatment) and 6C (for apical surface treatment).

In the basolateral context (n=2), the number of bacteria collected from the apical surface of human respiratory epithelia at 24 hours post-infection was significantly lower than the number of bacteria collected from the apical surface of human respiratory epithelia treated with diltiazem in basolateral medium (115 and 106 vs 76 and 106 CFU, respectively, *p<0.05).

In the context of apical treatment with diltiazem, a similar effect on Pseudomonas aeruginosa was observed at 24 hours post-infection (n=2), with a significant decrease in bacteria harvested from the apical surface of human respiratory epithelia treated with diltiazem compared with those untreated (87 and 106 versus 63.5 and 106 CFU, respectively).

On the whole, these results indicate that diltiazem treatment limits the replication of Pseudomonas aeruginosa in human respiratory epithelium.

Example 7. Treatment with Diltiazem Significantly Reduces the Multiplication of Human Metapneumovirus (hMPV)

Viral replication in reconstituted human epithelial models (MucilAir® HAE, Epithelix) of nasal origin was studied on epithelia treated or not treated with diltiazem. To that end, (i) fluorescence light microscopy photos were used to evaluate the efficacy and progression of the infection and (ii) quantification of the viral genome by RTqPCR was performed, on the one hand at the apical pole of the epithelium (surface harvesting) to quantify the excretion of viral progeny, and on the other hand in the total lysates of epithelial cells at end point (day 5 post-infection) to quantify intracellular viral replication within the epithelium.

Figure 7A:
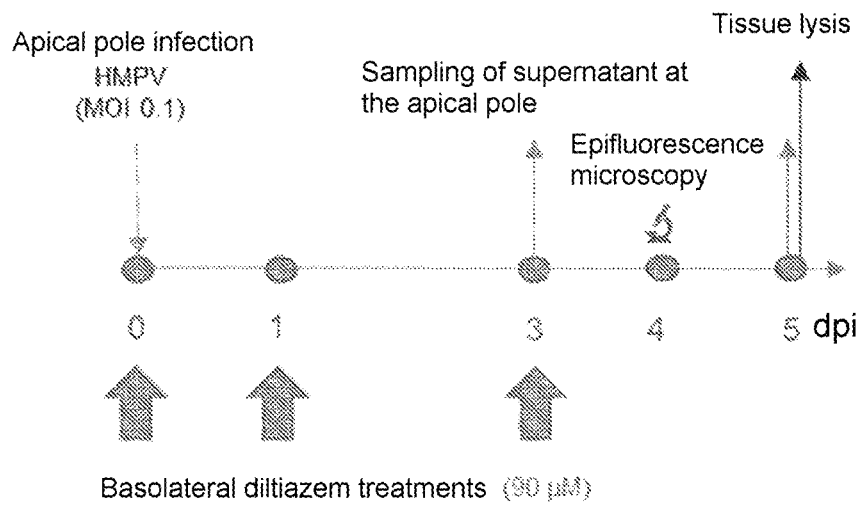

The chronogram of the experiment is presented in FIG. 7A.

Human respiratory epithelia (Mucilair, Epithelix) were infected with a recombinant hMPV-GFP virus (strain C-85473) at an MOI of 0.1, then treated (via the basolateral medium of the epithelia) or not with 3 successive doses of diltiazem at 90 µM at D0, D1 and D3 post-infection (3 epithelia per condition).

Figure 7B:
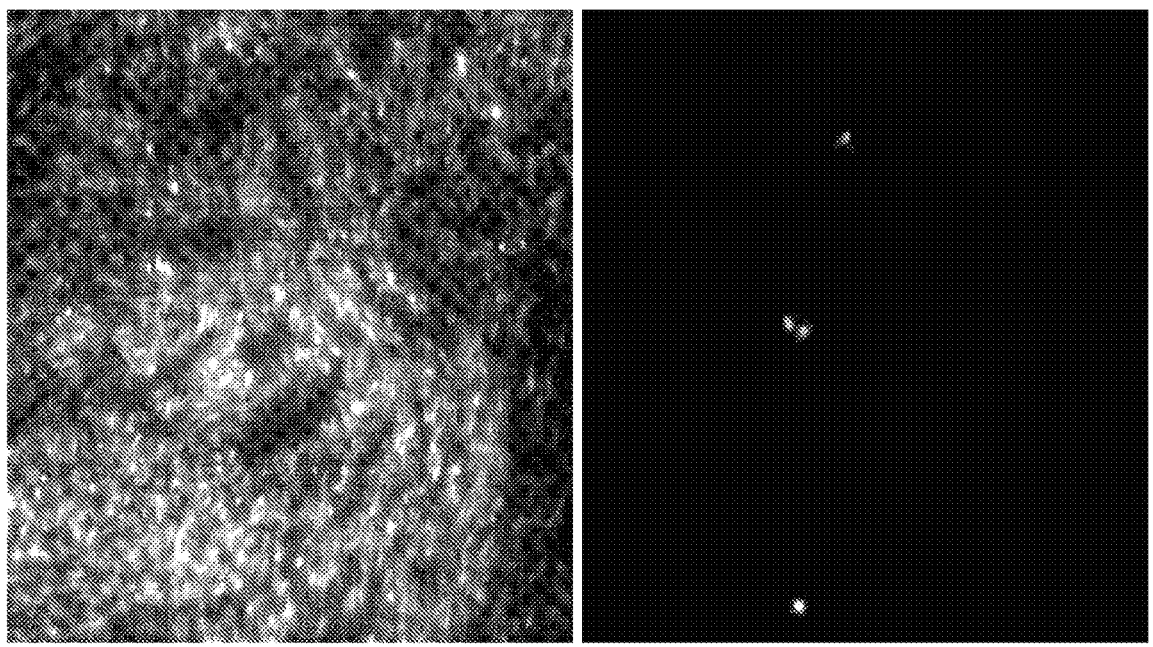

Epifluorescence microscopy observations were performed on D4 post-infection to observe the impact of diltiazem treatment on viral replication (FIG. 7B). Absent treatment, a fluorescence corresponding to the viral expression of GFP is observed on D4 post-infection in almost all the epithelium, whereas there are very few fluorescent cells in the infected epithelium treated with diltiazem at the same time post-infection.

Figure 7C:
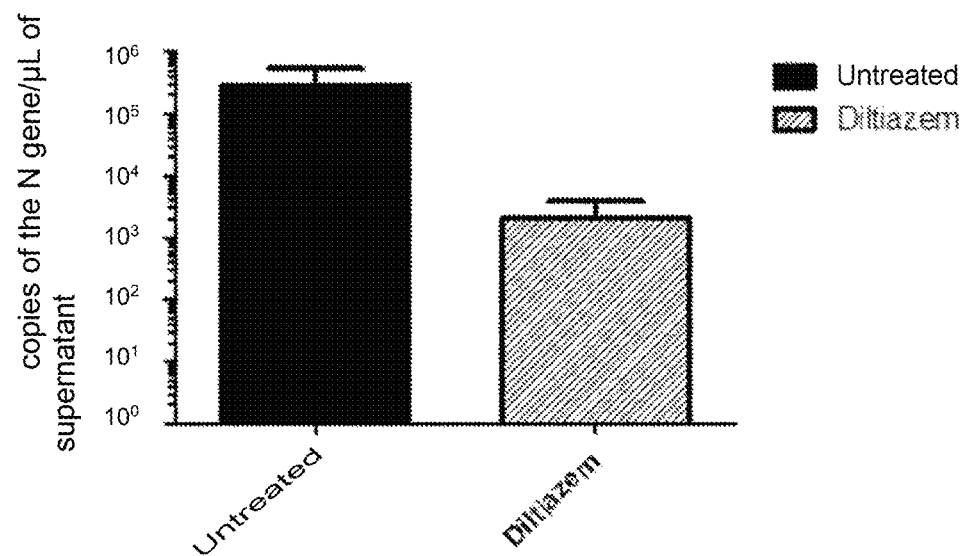

On day 3 post-infection, a wash at the apical pole of the infected epithelium, treated or not, was performed in order to harvest the viral progeny produced. The genomic viral RNA was extracted and quantified by RT-qPCR (Biosystems™ PowerUp™ SYBR™ Green, Thermo Fisher Scientific) using a plasmid containing the HMPV N gene. The results are expressed in copies of the N gene/µg RNA extracted (FIG. 7C).

qPCR results indicate that a very large amount of viral genome is present in apical pole supernatants harvested from untreated epithelia. This viral genome quantification reflects the level of viral progeny production following infection of the epithelia. In comparison, the amount of viral genome measured in apical supernatants collected from diltiazem-treated epithelia is significantly lower (2 log 10) (FIG. 7C).

Figure 7D:
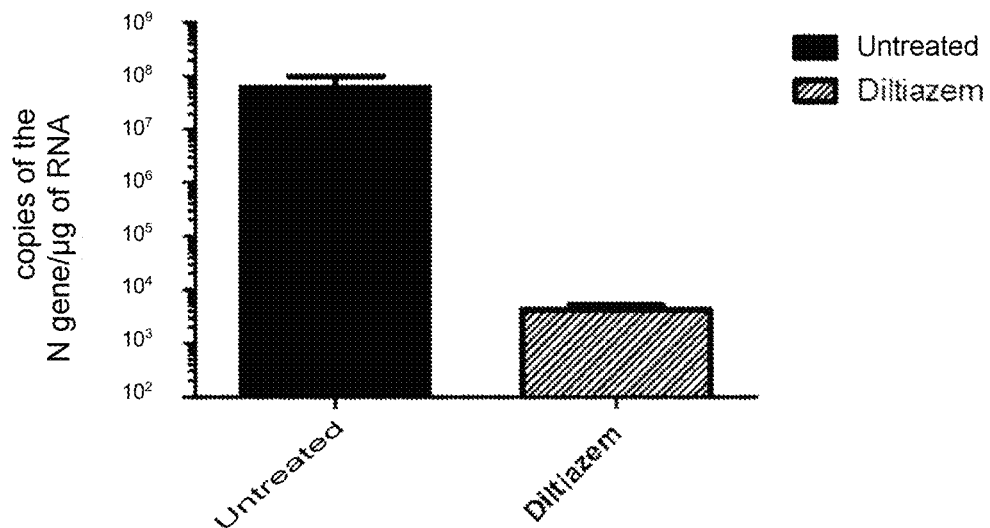

On day 5 post-infection, epithelial cells were harvested and lysed to extract total RNA. Total RNAs corresponding to the hMPV N viral gene were quantified by Rt-qPCR (Biosystems™ PowerUp™ SYBR™ Green, Thermo Fisher Scientific), using a range made from a plasmid containing the HMPV N gene. The results are expressed in copies of the N gene/µg RNA extracted (FIG. 7D).

qPCR results indicate that a very large amount of viral genome is present in untreated epithelia. On the other hand, the amount of viral genome is 4 log 10 lower in epithelia treated with diltiazem.

On the whole, these results indicate that diltiazem treatment significantly reduces hMPV viral replication.

Figure 8A:
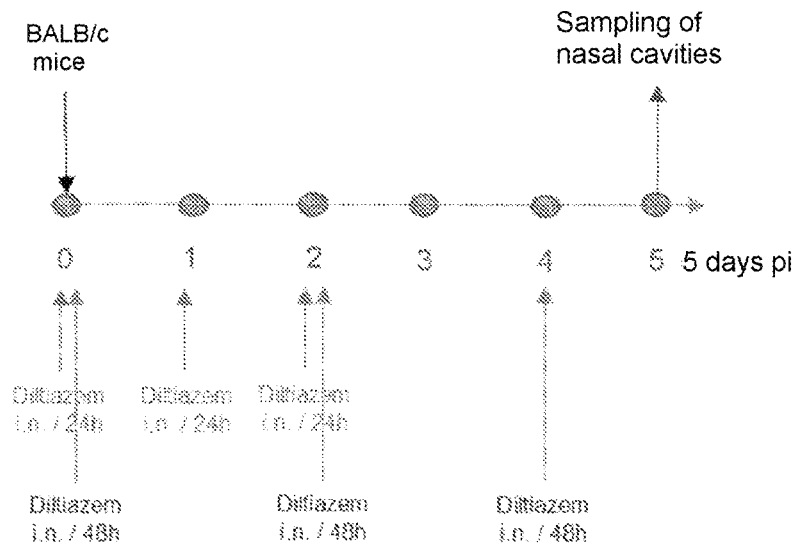

Example 8. In Vivo Diltiazem Induction of IFN-λ2 (IFNL2) Gene Expression Measured by RT-qPCR FIG. 8A schematically represents the chronology of treatments by intranasal (i.n.) instillation of BALB/c mice: the mice were treated (20 mg/kg) or not ("mock-treated" PBS control group) at day 0 (D0), then treated or not either daily on the following two days (D0, D1 and D2) or every 48 hours until day 4 (D0, D2 and D4). At D5, the nasal cavities were removed after euthanasia of the animals.

Total RNA was extracted from the samples using the RNeasy Kit (Qiagen) according to the supplier's instructions. After a reverse transcription step, a real-time quantitative PCR reaction was performed using the StepOnePlus™ Real-Time PCR System (Applied Biosystems), following the protocol described in the publication (Galani et al. Immunity 2017).

Figure 8B:
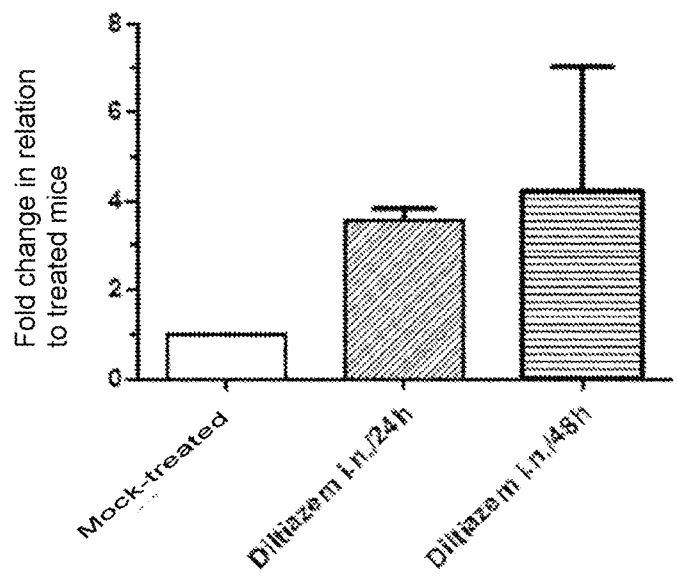

The expression of the IFN-λ2 gene (IFNL2) was measured by RT-qPCR, and is shown relative to the basal level (equal to 1) measured in untreated (Mock-treated) mice in FIG. 8B.

These results allow us to confirm that diltiazem administered intranasally in a mouse model also activates the IFN III pathway, as well as peros treatment.

REFERENCES

Patents

WO 02/094238
U.S. Pat. No. 4,605,552
WO 87/07508
WO 2011/066657
WO 2011/126071
WO 2016/146836
EP 1 117 408

BIBLIOGRAPHICAL REFERENCES

Andreakos E, Salagianni M, Galani I E, Koltsida O. *Interferon-λs: Front-Line Guardians of Immunity and Homeostasis in the Respiratory Tract.* Front Immunol. 2017 Sep. 29; 8:1232.

Galani I E, Triantafyllia V, Eleminiadou E E, Koltsida O, Stavropoulos A, Manioudaki M, Thanos D, Doyle S E, Kotenko S V, Thanopoulou K, Andreakos E. *Interferon-λ Mediates Non-redundant Front-Line Antiviral Protection against Influenza Virus Infection without Compromising Host Fitness.* Immunity. 2017 May 16; 46(5):875-890.e6.

Chan H L Y, Ahn S H, Chang T T, Peng C Y, Wong D, Coffin C S, Lim S G, Chen P J, Janssen H L A, Marcellin P, Serfaty L, Zeuzem S, Cohen D, Critelli L, Xu D, Wind-Rotolo M, Cooney E; LIRA-B Study Team. *Peginterferon lambda for the treatment of HBeAg-positive chronic hepatitis B: A randomized phase 2b study (LIRA-B).* J Hepatol. 2016 May; 64(5):1011-1019.

Davidson S, McCabe™, Crotta S, Gad H H, Hessel E M, Beinke S, Hartmann R, Wack A. *IFNλ is a potent anti-influenza therapeutic without the inflammatory side effects of IFNα treatment.* EMBO Mol Med. 2016 Sep. 1; 8(9):1099-112.

Donnelly R P, Kotenko S V. *Interferon-lambda: a new addition to an old family.* J Interferon Cytokine Res. 2010 August; 30(8):555-64.

Kotenko S V, Gallagher G, Baurin V V, Lewis-Antes A, Shen M, Shah N K, Langer J A, Sheikh F, Dickensheets H, Donnelly R P. *IFN-lambdas mediate antiviral protection through a distinct class II cytokine receptor complex.* Nat Immunol. 2003 January; 4(1):69-77.

O'Brien T R, Prokunina-Olsson L, Donnelly R P. *IFN-λ4: the paradoxical new member of the interferon lambda family.* J Interferon Cytokine Res. 2014 November; 34(11):829-38. doi: 10.1089/jir.2013.0136.

Galani I E(1), Triantafyllia V, Eleminiadou E E, Koltsida O, Stavropoulos A, Manioudaki M, Thanos D, Doyle S E, Kotenko S V, Thanopoulou K, Andreakos E. *Interferon-λ Mediates Non-redundant Front-Line Antiviral Protection against Influenza Virus Infection without Compromising Host Fitness.* Immunity. 2017 May 16; 46(5):875-890.e6. doi: 10.1016/j.immuni.2017.04.025.

The invention claimed is:

1. A method for treating an infection in an individual infected with a parainfluenza virus (hPIV), comprising the administration of diltiazem to said individual, to activate the expression of at least one gene encoding a type III interferon.

2. A method for treating an infection in an individual infected with the bacterium *Pseudomonas aeruginosa*, comprising the administration of diltiazem to said individual, to activate the expression of at least one gene encoding a type III interferon.

3. A method for treating a co-infection in an individual infected with at least one virus selected from human respiratory syncytial virus (hRSV), parainfluenza viruses (hPIV), human metapneumovirus (hMPV), and at least one bacterium, comprising the administration of diltiazem to said individual, to activate the expression of at least one gene encoding a type III interferon.

4. The method as claimed in claim 3, wherein said infection is a co-infection by human respiratory syncytial virus (hRSV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae*.

5. The method as claimed in claim 3, wherein said infection is a co-infection by a parainfluenza virus (hPIV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae*.

6. The method as claimed in claim 3, wherein said infection is a co-infection by a human metapneumovirus (hMPV) and at least one bacterium of a species selected from *Enterococcus faecalis, Borrelia burgdorferi, Listeria monocytogenes, Mycobacterium tuberculosis, Pseudomonas aeruginosa, Staphylococcus aureus, Staphylococcus epidermidis, Salmonella typhimurium, Streptococcus pneumoniae* and *Haemophilus influenzae*.

* * * * *